United States Patent
Blye et al.

(10) Patent No.: US 7,820,642 B2
(45) Date of Patent: Oct. 26, 2010

(54) NANDROLONE 17β-CARBONATES

(75) Inventors: Richard P. Blye, Highland, MD (US);
Hyun K. Kim, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 565 days.

(21) Appl. No.: 11/815,532

(22) PCT Filed: Jan. 24, 2006

(86) PCT No.: PCT/US2006/002436

§ 371 (c)(1),
(2), (4) Date: Aug. 29, 2007

(87) PCT Pub. No.: WO2006/083618

PCT Pub. Date: Aug. 10, 2006

(65) Prior Publication Data

US 2008/0167283 A1     Jul. 10, 2008

Related U.S. Application Data

(60) Provisional application No. 60/650,376, filed on Feb. 4, 2005.

(51) Int. Cl.
*A61K 31/56* (2006.01)
*C07J 1/00* (2006.01)

(52) U.S. Cl. .......................... 514/179; 552/646; 552/647

(58) Field of Classification Search ................. 552/646, 552/647; 514/179
See application file for complete search history.

(56) References Cited

U.S. PATENT DOCUMENTS

| | | | |
|---|---|---|---|
| 3,056,727 A | 10/1961 | Allais et al. |
| 3,314,856 A | 4/1967 | Allais et al. |
| 3,515,720 A | 6/1970 | Scribner |
| 3,523,126 A | 8/1970 | Boswell |
| 3,629,244 A | 12/1971 | Costerousse |
| 3,637,771 A | 1/1972 | Nedelec et al. |
| 3,862,195 A | 1/1975 | Gastaud |
| 5,952,319 A | 9/1999 | Cook et al. |
| 6,369,047 B2 | 4/2002 | Cook et al. |
| 6,670,352 B2 | 12/2003 | Cook et al. |
| 2002/0002156 A1 | 1/2002 | Cook et al. |
| 2002/0103177 A1 | 8/2002 | Cook et al. |
| 2003/0069215 A1 | 4/2003 | Blye et al. |
| 2003/0130243 A1 | 7/2003 | Blye et al. |

FOREIGN PATENT DOCUMENTS

| | | |
|---|---|---|
| GB | 1291293 | 5/1970 |
| WO | WO 01/74839 A2 | 10/2001 |

OTHER PUBLICATIONS

Muddana et al., "11beta-alkyl-Delta9-19-nortestosterone derivatives: high-affinity ligands and potent partial agonists of the androgen receptor," *J. Med. Chem.*, 47, 4985-4988 (2004).

*Primary Examiner*—Barbara P Badio
(74) *Attorney, Agent, or Firm*—Leydig, Voit & Mayer, Ltd.

(57) ABSTRACT

Disclosed are compounds of the formula (I)

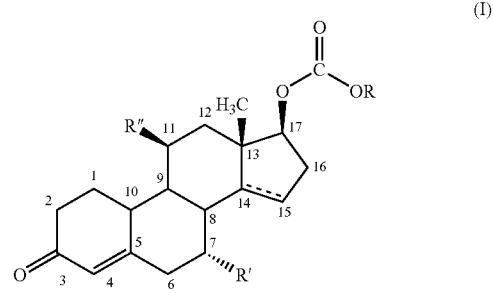

wherein R is $C_1$-$C_{30}$ alkyl, which may be optionally further substituted with one or more of $C_5$-$C_8$ cycloalkyl groups, or a $C_5$-$C_{12}$ cycloalkyl, which may be optionally substituted with one or more $C_1$-$C_{30}$ alkyl groups, R' is hydrogen or lower alkyl, R" is a $C_1$-$C_{30}$ alkyl or halo, and the bond between C14 and C15 can be a single bond or double bond. Also disclosed are pharmaceutical compositions comprising such compounds and methods of use thereof. These compounds can find use in treating a number of diseases or conditions such as hypogonadism, osteoporosis, and anemia, in providing hormonal therapy and contraception, as an anabolic agent, and in suppressing the release of hormones such as the luteinizing hormone.

62 Claims, 17 Drawing Sheets

2a  R = -CH₃
2b  R = -(CH₂)₅CH₃
2c  R = -(CH₂)₉CH₃
2d  R = -(CH₂)₁₁CH₃

4a R = -CH₃
4b R = - (CH₂)₉CH₃
4c R = -Adamantyl

11a X = F, R = Decyl
11b X = F, R = Dodecyl
11c X = F, R = Methyl
12a X = Cl, R = Decyl
12b X = Cl, R = Dodecyl
12c X = Cl, R = Methyl

NANDROLONE 17β-CARBONATES

FIELD OF THE INVENTION

This invention pertains to androgenic compounds, particularly 17β-carbonates of 19-nortestosterone, pharmaceutical compositions, and methods of use thereof.

BACKGROUND OF THE INVENTION

Androgens are used in hormonal therapy. Androgens are administered as part of any hormonally-based male contraceptive since suppression of the hypophyseal-gonadal axis by progestational steroids or analogs of GnRH (gonadotropin releasing hormone) affects both the gametogenic and endocrine function of the testis. Androgens are indicated in the treatment of hypogonadism irrespective of the cause and have become the subject of intense interest in hormone replacement therapy (HRT) for both men and women.

The principal male hormone, testosterone, is responsible for the development of the male body habitus, secondary sexual characteristics, libido and potentia as well as the processes of spermatogenesis. Testosterone is a steroid produced by the testis and exhibits an extremely short half-life. It is only weakly active by oral administration. Consequently, the natural hormone finds limited use in therapeutic medicine where androgen supplementation is desired.

A number of synthetic androgens have been prepared over the last fifty years including esters of the free alcohol which exhibit varying durations of activity following a single intramuscular injection. Notable among these is testosterone enanthate, which is used extensively for replacement therapy in hypogonadal men and as the androgenic component of several experimental male contraceptives. However, it must be administered at biweekly intervals in order to maintain testosterone levels in the normal range. Other 17-esters of testosterone are being developed as a long-acting injectable androgen. Like testosterone enanthate, these products are administered in an oily vehicle and have limited duration of action.

The development of oral formulations of androgenic steroids has been less successful. The most widely used commercial preparation is methyltestosterone which unfortunately, is associated with hepatotoxicity upon chronic administration. Therapeutic uses of androgens for replacement therapy usually require long-term treatment, thus precluding utilization of 17-alkylated steroids with their associated toxicity. Testosterone undecanoate also has been marketed as an oral androgen but, like testosterone, it is rapidly metabolized by the liver and must be administered several times a day, which may be inconvenient to the patient.

The foregoing shows that there exists a need for androgenic agents with long-acting activity, particularly long-acting oral activity. The advantages of the invention, as well as inventive features, will be apparent from the description of the invention provided herein.

BRIEF SUMMARY OF THE INVENTION

The invention provides androgenic compounds, particularly nandrolone carbonates of the formula

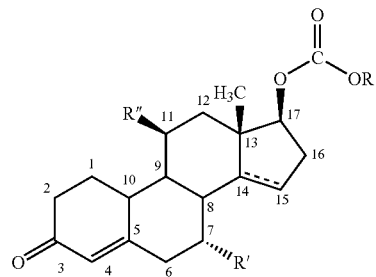

wherein R is an alkyl group which may be optionally further substituted with one or more cycloalkyl groups or a cycloalkyl group which may be optionally substituted with one or more alkyl groups; R' is hydrogen or a lower alkyl; R" is an alkyl group or halo; and the bond between C14 and C15 can be a single bond or double bond.

The invention also provides pharmaceutical compositions comprising such compounds, and methods of use thereof. The compounds of the invention can find use in treating a number of diseases or conditions such as hypogonadism, osteoporosis, and anemia, in providing hormonal therapy and contraception, as an anabolic agent, and in suppressing the release of hormones such as the luteinizing hormone.

DETAILED DESCRIPTION OF THE INVENTION

Figure 1:
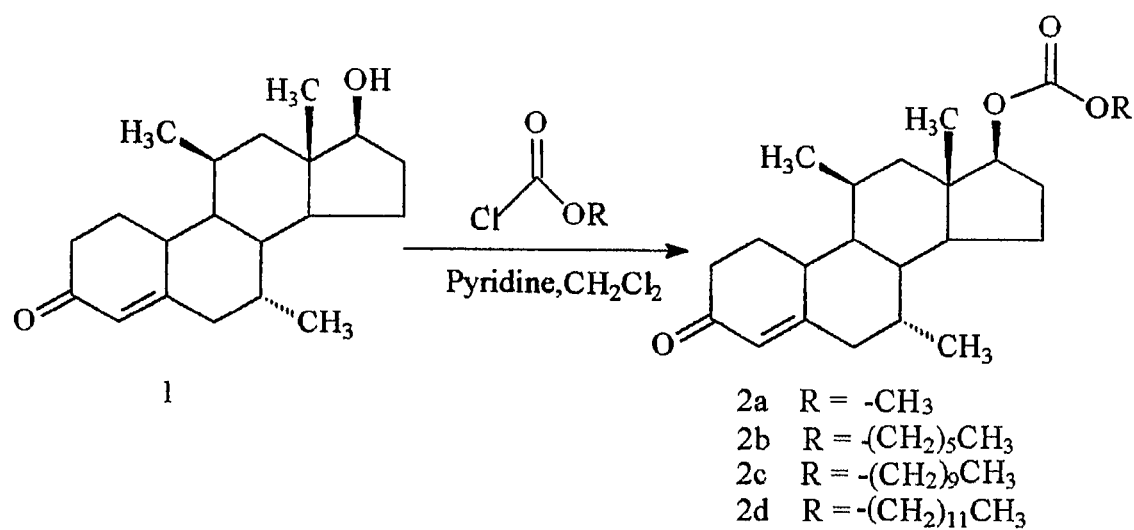
FIG. 1 depicts a reaction scheme to prepare dimethandrolone carbonates 2a-2d in accordance with an embodiment of the invention. Compound 1 is dimethandrolone.

The present invention provides, in an embodiment, compounds of formula (I):

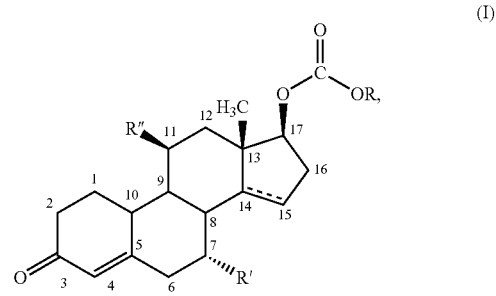

wherein R is $C_1$-$C_{30}$ alkyl which may be optionally further substituted with one or more $C_5$-$C_8$ cycloalkyl groups or $C_5$-$C_{12}$ cycloalkyl which may be optionally substituted with one or more $C_1$-$C_{30}$ allyl groups; R' is hydrogen or lower allyl; R" is $C_1$-$C_{30}$ alkyl or halo; and the bond between C14 and C15 can be a single bond or double bond. When R' is hydrogen, there is no stereochemistry at C7.

Specifically, R can be $C_1$-$C_{18}$ alkyl, and more specifically $C_1$-$C_{12}$ alkyl. In an embodiment, R" is $C_1$-$C_{30}$ alkyl, specifically $C_1$-$C_6$ alkyl, and more specifically methyl or ethyl. In an embodiment, R' can be a lower allyl, e.g., one having a $C_1$-$C_4$ alkyl group, particularly, methyl or ethyl.

The alkyl group, in accordance with the present invention, can be linear or branched. Examples of alkyl groups include methyl, ethyl, n-propyl, i-propyl, n-butyl, i-butyl, t-butyl, pentyl, hexyl, heptyl, octyl, nonyl, decyl, undecyl, dodecyl, tridecyl, tetradecyl, pentadecyl, and the like.

The cycloalkyl group, in accordance with the present invention, can be mono, bi, or tricyclic. Examples of cycloalkyl groups include cyclopropyl, cyclobutyl, cyclopentyl, cyclohexyl, cycloheptyl, cyclooctyl, bornyl, norbornyl, bicyclooctyl, bicyclononyl, adamantyl, tricyclodecanyl, and the like.

In a specific embodiment, the present invention provides compounds wherein R' is methyl or ethyl, e.g., R' is methyl or ethyl and R" is a $C_1$-$C_{30}$ alkyl.

In an embodiment of the invention, R is $C_1$-$C_{30}$ alkyl, specifically $C_1$-$C_{18}$ alkyl, and more specifically, $C_1$-$C_{12}$ alkyl. In another embodiment, R is a cycloalkyl group, optionally substituted with an alkyl group, for example, a cyclohexyl group substituted with a butyl group (e.g., trans-4-n-butylcyclohexyl).

In accordance with an embodiment of the invention, the bond between C14 and C15 is a single bond. For example, the bond between C14 and C15 is a single bond and R' is hydrogen. Examples of compounds of the embodiment include 11β-ethyl-19-nortestosterone-17-methylcarbonate, 11β-ethyl-19-nortestosterone-17-decylcarbonate, 11β-ethyl-19-nortestosterone-17-dodecylcarbonate, 11β-methyl-19-nortestosterone-17-methylcarbonate, and 11β-methyl-19-nortestosterone-17-decylcarbonate.

In another embodiment of the invention, R" is a halogen, e.g., fluoro, chloro, bromo, or iodo. For example, the bond between C14 and C15 is a single bond and R" is halogen, particularly where R is a $C_1$-$C_{12}$ alkyl. Examples of compounds of the embodiment include 11β-fluoro-19-nortestosterone-17-decylcarbonate, 11β-fluoro-19-nortestosterone-17-dodecylcarbonate, 11β-chloro-19-nortestosterone-17-decylcarbonate, and 11β-chloro-19-nortestosterone-17-dodecylcarbonate.

In accordance with another embodiment of the invention, R' is methyl or ethyl and R" is methyl or ethyl, and the bond between C14 and C15 is a single bond, particularly where R is a $C_1$-$C_{12}$ alkyl group or a $C_3$-$C_8$ cycloalkyl group optionally substituted with an alkyl group. Examples of such compounds include 7α-methyl, 11β-ethyl-19-nortestosterone-17-methylcarbonate, 7α-methyl, 11β-ethyl-19-nortestosterone-17-decylcarbonate, 7α-methyl, 11β-ethyl-19-nortestosterone-17-hexylcarbonate, 7α-methyl, 11β-ethyl-19-nortestosterone-17-dodecylcarbonate, 7α,11β-dimethyl-19-nortestosterone-17-methylcarbonate, 7α,11β-dimethyl-19-nortestosterone-17-hexylcarbonate, 7α,11β-dimethyl-19-nortestosterone-17-decylcarbonate, 7α,11β-dimethyl-19-nortestosterone-17-dodecylcarbonate, 7α-ethyl, 11β-methyl-19-nortestosterone-17-methylcarbonate, 7α-ethyl, 11β-methyl-19-nortestosterone-17-hexylcarbonate, 7α-ethyl, 11β-methyl-19-nortestosterone-17-decylcarbonate, 7α-ethyl, 11β-methyl-19-nortestosterone-17-dodecylcarbonate, 7α,11β-diethyl-19-nortestosterone-17-methylcarbonate, 7α,11β-diethyl-19-nortestosterone-17-hexylcarbonate, 7α,11β-diethyl-19-nortestosterone-17-decylcarbonate, 7α,11β-diethyl-19-nortestosterone-17-dodecylcarbonate, 11β-methyl-19-nortestosterone-17-(trans-4-n-butylcyclohexyl) carbonate, and 7α,11β-dimethyl-19-nortestosterone-17-(trans-4-n-butylcyclohexyl) carbonate.

In accordance with yet another embodiment of the invention, R' is methyl and R" is halogen, and the bond between C14 and C15 is a single bond, particularly where R' is a $C_1$-$C_{12}$ alkyl. Examples of such compounds include 7α-methyl, 11β-fluoro-19-nortestosterone-17-decylcarbonate, 7α-methyl, 11β-fluoro-19-nortestosterone-17-dodecylcarbonate, 7α-methyl, 11β-chloro-19-nortestosterone-17-decylcarbonate, and 7α-methyl, 11β-chloro-19-nortestosterone-17-dodecylcarbonate.

In accordance with another embodiment, R' is hydrogen and R" is halogen, and the bond between C14 and C15 is a single bond, particularly where R is a cycloalkyl group substituted with an alkyl; for example, the compound is 11β-fluoro-19-nortestosterone-17-(trans-4-n-butylcyclohexyl) carbonate.

In accordance with a further embodiment of the invention, the bond between C14 and C15 is a single bond and R is decyl or dodecyl. In accordance with another embodiment of the invention, the bond between C14 and C15 is a single bond and R" is methyl or ethyl. In accordance with yet another embodiment of the invention, the bond between C14 and C15 is a single bond and R" is a halogen, particularly chloro or fluoro.

In accordance with an embodiment, the present invention provides compounds wherein R is a $C_5$-$C_{12}$ cycloalkyl, particularly wherein the cycloalkyl is a tricycloalkyl, such as a $C_{10}$ tricycloalkyl. In a specific embodiment of these compounds, the bond between C14 and C15 is a double bond. An example of such a compound is 7α,11β-dimethyl-14-dehydro-19-nortestosterone-17-adamantylcarbonate.

In a specific embodiment of the invention, the bond between C14 and C15 is a double bond and R is $C_1$-$C_{18}$ alkyl, particularly $C_1$-$C_{12}$ alkyl, for example, methyl or decyl.

Examples of the alkyl group substituted with a cycloalkyl group, in accordance with the present invention, can be cyclohexylmethyl, cyclopentylmethyl, cyclohexylethyl, norbornylmethyl, adamantylmethyl, norbornylethyl, adamantylethyl, and the like.

Examples of the cycloalkyl group substituted with an alkyl group, in accordance with the present invention, can be methylcyclopentyl, ethylcyclopentyl, propylcyclopentyl, butylcyclopentyl, methylcyclohexyl, ethylcyclohexyl, propylcyclohexyl, butylcyclohexyl, and the like.

The present invention further provides a pharmaceutical composition comprising a compound of the invention and a pharmaceutically acceptable carrier.

The pharmaceutically acceptable carriers described herein, for example, vehicles, adjuvants, excipients, or diluents, are well known to those who are skilled in the art and are available to the public. It is preferred that the pharmaceutically acceptable carrier be one which is chemically inert to the active compounds and one which has no detrimental side effects or toxicity under the conditions of use.

The choice of carrier will be determined in part by the particular compound (active agent), as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting A pharmaceutically acceptable carrier is advantageously combined with each active to ease the administration of the compound to a patient in need. Suitable carriers for oral and buccal dosage forms, such as tablets, capsules, caplets and soft gelcaps (having an oily carrier), are well known, and may be used in connection with the compounds. Preferably, oral dosage formulations of the actives include an oily carrier, and are provided in the form of a soft gelcap, as this formulation was found to enhance the beneficial properties of the actives upon oral administration. Illustrative of oily substances that may be used to provide an oily carrier include, but are not limited to, vegetable oils, e.g. olive oil, safflower oil, corn oil, sunflower oil, cotton seed oil, tsubaki oil, rice bran oil, soybean oil, sesame oil, wheat germ oil, coconut oil, peanut oil, rape seed oil and the like, fish oils, e.g., cuttlefish oil, cod oil, and the like, liver oils, e.g., shark liver oil, cod liver oil and the like, blubber oils, e.g., seal oil, blue whale oil, etc.), conchiferous oils, e.g., abalone oil, oyster oil, and the like, medicinal oily substances, e.g., castor oil, fatty acid glycerides, vitamin E, vitamin A, vitamin K, and the like, polyethylene glycol and the like, and mixtures thereof.

Formulations suitable for oral administration can comprise (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

For parenteral administration, any type of carrier that maintains the benefits of the invention as described herein may be used. Preferably, the compounds of the invention are suspended in an aqueous carrier suitable for injection. The water component of the aqueous carrier should constitute at least half thereof, on a weight percent basis, preferably at least about 80 wt. %, and more preferably at least about 90 wt. % of the aqueous carrier. Illustrative of a preferred parenteral formulation is one that includes up to 300 mg of the compound suspended in about 1 ml of an aqueous carrier. An illustrative aqueous carrier may be prepared by combining: 1 g benzyl alcohol, 0.5 g sodium carboxyethyl cellulose 50, 0.376 g disodium hydrogen phosphate dihydrate, 1.495 g sodium dihydrogen phosphate dihydrate, with water for injection (WFI) being added to bring volume of the aqueous carrier up to 100 ml.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl diallyl ammonium halides, and allyl pyridinium halides, (b) anionic detergents such as, for example, alkyl, aryl, and olefin sulfonates, allyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof. Suitable preservatives and buffers can be used in such formulations. In order to minimize or eliminate irritation at the site of injection, such compositions may contain one or more nonionic surfactants. The quantity of surfactant in such formulations typically ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, eds., pages 238-250 (1982), and *ASHP Handbook on Injectable Drugs*, Toissel, 4th ed., pages 622-630 (1986).

When formulated as an injectable, the compound may be provided in any suitable form, e.g., lyophilizate, dry powder for reconstitution, a ready-to-use liquid, and in any suitable container, e.g., vial, pre-filled syringe, or the like. The compounds may also be administered transdermally or subcutaneously. Transdermal delivery devices are well known. Illustrative transdermal devices are described in U.S. Pat. Nos. 5,635,203 and 6,024,976. When a transdermal delivery device is used, the amount of the active included in the device for therapy should range from about 5% to about 25% of the parenteral dose, and preferably from about 10% to about 20% of that dose, as set forth herein Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

In a specific embodiment, the pharmaceutical composition is suitable for oral or administration. For example, the pharmaceutical composition comprises 7α,11β-dimethyl-19-nortestosterone-17-decylcarbonate and a pharmaceutically acceptable carrier, wherein the composition is suitable for oral administration. In a further example, the pharmaceutical composition 7α,11β-dimethyl-19-nortestosterone-17-methylcarbonate or 7α,11β-dimethyl-19-nortestosterone-17-hexylcarbonate and a pharmaceutically acceptable carrier, wherein the composition is suitable for subcutaneous injection. In another example, the pharmaceutical composition comprises an aqueous crystalline suspension of 7α,11β-dimethyl-19-nortestosterone-17-decylcarbonate, wherein the composition is suitable for subcutaneous injection.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired. In proper doses and with suitable administration of certain compounds, the present invention provides for a wide range of responses. Typically the dosages range from about 0.001 to about 1000 mg/kg body weight of the animal being treated per day. Preferred dosages range from about 0.01 to about 10 mg/kg body weight/day, and further preferred dosages range from about 0.01 to about 1 mg/kg body weight/day.

The present invention further provides a method for treating a male patient for hypogonadism comprising administering an effective amount of a compound of the invention. Any suitable hypogonadism can be treated, for example, the hypogonadism is selected from the group consisting of hypogonadotropic eunuchoidism, fertile eunuch syndrome, prepubertal panhypopituitarism, and postpubertal pituitary failure, and any combination thereof.

The present invention further provides a method for treating a male patient for hypogonadism comprising administering an effective amount of a compound of the invention. Any suitable hypogonadism can be treated, for example, the hypogonadism can be selected from the group consisting of Klinefelter's syndrome, Reifenstein's syndrome, functional prepubertal castration syndrome, male "Turner's syndrome", Sertoli cell-only syndrome, adult seminiferous tubule failure, and adult Leydig cell failure, and any combination thereof.

The present invention further provides a method for providing hormonal therapy to a patient comprising administering an effective amount of a compound of the invention. The present invention also provides a method for providing a contraceptive to a male comprising administering to the male an effective amount of a compound of the invention. The present invention also provides a method for treating a patient with osteoporosis comprising administering an effective amount of a compound of the invention. The present invention further provides a method for treating a patient with anemia comprising administering an effective amount of a compound of the invention. The present invention also provides a method for treating a patient in need of an anabolic agent comprising administering an effective amount of a compound of the invention. The patient in need of anabolic agent may be one afflicted with a muscle wasting disease, e.g., AIDS, or a patient in need of anabolic agent may be one having low muscle mass, or the patient is afflicted with cancer. The present invention also provides a method for suppressing the release of luteinizing hormone in a mammal comprising administering to the mammal an effective amount of the compound of the invention, particularly 7α,11β-dimethyl-19-nortestosterone-17-decylcarbonate. The serum level of the hormone remains suppressed for both groups of animals during the administration of the drug. When the administration of the drug is discontinued, the hormone level, as expected, bounces back and increases beyond the pretreatment level (at week −1 or 0) for the ester drug. Thus, for example, the hormone level can be suppressed up to several weeks, e.g., from about 2 to about 20 weeks or more. This could have advantageous clinical implications, for example, in obtaining sustained suppression of the luteinizing hormone or hormone replacement therapy. In addition, this could have an advantage by providing a facile treatment using oral compositions such as tablets or capsules of the carbonates of the invention in suppressing hormone levels. Such treatment can be advantageous relative to a treatment involving parenteral (e.g., subcutaneous) administration of a drug such as the ester drug. Patient compliance can be better with oral formulations than injections.

By way of example only, and without intending to limit the therapeutic uses of the actives, the compounds may be used in the treatment of hypogonadal males, e.g., hypogonadatrophic eunuchoidism (complete, incomplete, delayed puberty), fertile eunuch, prepubertal panhypopituitarism, postpubertal pituitary failure (selective, panhypopituitarism). The compounds may also be administered (either alone or, more effectively, in combination with one or more steroidal progestins or estrogens) to induce and maintain fertility suppression in male animals, or as an androgenic component for feedback. Further, and due to their anabolic properties, the compounds may be administered to promote and maintain muscle growth and maintenance. These properties can be particularly important in persons afflicted with muscle wasting diseases such as AIDS, but are more generally applicable to the elderly who typically have relatively low muscle mass. In addition, the compounds may be used for the treatment of cancer, e.g., the palliative treatment of breast cancer in men and women, the treatment of osteoporosis, anemia, anabolism, hormonal replacement therapy (in males and females) and hypogonadotrophic conditions (e.g., Klinefelter's, Reifenstein's, functional prepubertal castration syndrome, male Turner's syndrome, Sertoli cell-only syndrome, adult seminiferous tubule failure (e.g., mumps orchitis, irradiation, idiopathic, myotonia dystrophica), and adult Leydig cell failure).

As a general statement, the effective oral dosage of any of the compounds for any hormone replacement therapy which requires an androgen, e.g., the treatment of hypogonadism, will be the inverse of its potency ratio relative to the amount of the standard required to provide the same effect, e.g., the amount of methyltestosterone administered orally required to provide the same effect. For example, in the case of hypogonadism, the compound may be orally administered in therapeutically effective amounts. For example, the oral dosage may range from about 1 mg/day to about 75 mg/day, such as from about 2 mg/day to about 50 mg/day, and specifically from about 1 mg/day to about 25 mg/day. For the treatment of cancer, e.g., breast cancer in women, the amount of the compound administered can vary, but can range from at least about 10 mg/day, specifically at least about 25 mg/day, and more specifically, at least about 50 mg/day.

In the use of the compounds for male contraception, amounts effective to provide such therapy may be administered. Generally, the effective oral doses may vary, but can range from about 1 to about 50 mg per day. Of course, the greater the relative potency, the lesser the dose, for example, an effective oral dose may range from about 1 mg/day to about 25 mg/day, advantageously from about 2 mg/day to about 20 mg/day, and up to about 15 mg/day.

In the case of conditions requiring chronic hormonal therapy, such as hypogonadism, the compound may be dispersed in an aqueous vehicle and may be administered as an aqueous formulation at lower doses compared to both testosterone enanthate (in an oily carrier) and testosterone bucyclate, and at relatively long intervals. More specifically, and by further way of comparative example, doses of the compound, when dispersed in an aqueous formulation, may generally range from about one-third to about three-quarters the dose of testosterone enanthate (provided in a sesame oil carrier) required to provide substantially equivalent therapeutic results, with between about one-half and about two-thirds of that latter dose being preferred.

Because of its long-acting androgenic activity, particularly when administered parenterally in an aqueous carrier in effective amounts, the compound may be administered at intervals equal to, or in excess of, about two weeks. More specifically, they may be administered at intervals of about one month, preferably about two months, more preferably once about every three months or about every two to four months. This provides a significant advantage to a patient relative to existing regimens that require therapeutic injections on a more frequent basis.

For example, in treating hypogonadism, those compounds may be formulated in an aqueous carrier and provide therapeutic benefits over an extended time period may be administered in amounts ranging from about 1 mg up to about 100 mg about every two weeks, and advantageously from about 25 to about 75 mg during that period; up to about 200 mg about every month, and advantageously from about 50 mg to about 150 mg during that time period; up to about 400 mg about every 2 months, and advantageously from about 100 to about 300 mg during that time period; and up to about 600 mg about every 3 months, and advantageously from about 150 mg to about 450 mg during that time period. These dosages, advantageously provided by a single injection at the beginning of each time period, are less than the dosages of testosterone enanthate and testosterone bucyclate that may be used to provide similar therapeutic effects over the same periods.

By way of further example, doses of the compounds of the invention effective for male contraception via parenteral administration, if used alone, may range from about 25 mg/week up to about 200 mg/week, advantageously up to about 150 mg/week, and preferably from about 50 mg/week to about 100 mg/week. If used in a more typical manner, i.e., combined with estrogen and/or progestins, parenteral dosages of the foregoing actives may range from about 1 mg up to about 100 mg every about two weeks, advantageously from about 2 mg up to about 75 mg, and preferably up to about 50 mg, every two weeks. Of course, because of the long-acting activity of these actives, these dosages may be administered on a substantially linear basis if activity beyond the periods set forth above is desired.

The enhanced potency of the compounds of the invention advantageously permits a further advantage in that effective amounts may be administered via a single injection, which is desirable from a patient comfort and cost perspective. Equivalent therapeutic results using testosterone enanthate would require multiple injections. Of course, multiple injections of relatively lower doses of the inventive actives may be administered if required or desired. For example, actives formulated into an oily carrier, despite relatively high potency, need to be administered more frequently to obtain the desired therapy, with the dose being adjusted based upon the particular active's potency in that carrier.

The synthesis of dimethandrolone has been described in International Patent Publication Number WO 01174839 A2.

The following examples further illustrate the invention but, of course, should not be construed as in any way limiting its scope.

EXAMPLE 1

This example illustrates a method for preparing compounds in accordance with an embodiment of the invention.

The syntheses of the 17β-methyl, hexyl, decyl and dodecyl carbonates of dimethandrolone were carried out following the procedure described below by treatment of dimethandrolone and the corresponding alkyl chloroformates in the presence of pyridine in dichloromethane, as described below.

17β-Methoxycarbonyloxy-7α,11β-dimethylestr-4-en-3-one (2a, CDB-4718): A solution of the dimethandrolone (1 (FIG. 1), 1.0 g, 3.31 mmol) in dry $CH_2Cl_2$ (50 mL) under nitrogen, was cooled to 0° C. in an ice bath. Pyridine (1 mL, 12.4 mmol) followed by methyl chloroformate (1 mL, 12.9 mmol) was added and the mixture stirred at 0° C. for about 15 min and allowed to warm to room temperature. The reaction mixture was stirred at room temperature for one hour after which time TLC (5% acetone in $CH_2Cl_2$) indicated about 60% reaction. The reaction mixture was cooled to 0° C., and treated with additional pyridine (1 mL) and methyl chloroformate (1 mL). Upon warming to room temperature, evolution of gas was observed. After stirring at room temperature overnight, TLC (5% acetone in $CH_2Cl_2$) indicated about 80% reaction. Solvents were removed in vacuo under a stream of dry nitrogen and the residue was dissolved in $CH_2Cl_2$ and washed with $H_2O$ (3×). The organic fractions were filtered through anhydrous $Na_2SO_4$, combined and concentrated in vacuo to give 1.3 g of the residue as yellow foam. This material was purified by Flash chromatography (3% acetone in $CH_2Cl_2$) followed by crystallization from methanol to give >0.74 g of the pure product 2a in 62% yield; m.p.=153-154° C. Analysis by HPLC on NovaPak C-18 column, Waters Assoc eluted with $CH_3CN:H_2O$ in a ratio of 7:3 at a flow rate of 1 mL/min and at λ=240 nm indicated compound 2a to be >99% pure with a retention time of 4.62 min. FTIR (ATR), vmax 2958, 2939, 2883, 1739, 1663 and 1620 $cm^{-1}$.

$^1$H NMR (300 MHz, $CDCl_3$): δ 0.786 (d, 3H, J=6.97 Hz, C7α-$CH_3$), 0.953 (s, 3H, Cf18-$CH_3$), 1.062 (d, 3H, J=7.2 Hz, C11β-$CH_3$), 3.775 (s, 3H, —C(O)$OCH_3$), 4.479 (dd, 1H, J=9 Hz, J=7.4 Hz, C17α-H) and 5.852 (s, 1H, C4-CH=) ppm. $^{13}$C NMR (300 MHz, $CDCl_3$): δ 12.881 (C7-$CH_3$), 15.117 (C18-$CH_3$), 17.084 (C11β-$CH_3$), 22.642, 26.404, 27.175, 28.416, 30.726, 36.638, 36.781, 38.702, 42.669, 43.255, 44.571, 45.736, 47.635, 54.594 (OCH$_3$), 87.352 (C17), 126.585 (C4), 155.773 (O—C=O), 165.533 (C5), and 199.421 (C3) ppm.

MS (El) m/z (relative intensity): 360 (M+, 53), 284(99), 175 (100), and 147 (49).

Anal. Calcd. for C$_{22}$H$_{32}$O$_4$: C, 73.30; H, 8.95. Found: C, 73.21; H, 9.01.

17β-Hexyloxycarbonyloxy-7α,11β-dimethylestr-4-en-3-one (2b, CDB-4731): Following the procedure in a manner similar to that of the above for the preparation of 2a, dimethandrolone (1, 1.0 g, 3.31 mmol) in dry CH$_2$Cl$_2$ (50 mL) was reacted with hexyl chloroformate (2 mL, 12.2 mmol) in the presence of pyridine (1 mL, 12.4 mmol) to give 1.6 g of the crude hexyl carbonate (2b). Purification by flash chromatography using 2% acetone in CH$_2$Cl$_2$ followed by crystallization from pentane gave 1.2 g of the pure product 2b in 84.3% yield; m.p.=60.4-61.1° C. Analysis by HPLC on NovaPak C-18 column, Waters Assoc, eluted with 100% CH$_3$CN at a flow rate of 1 mL/min and at λ=240 nm indicated compound 2b to be >99% pure with a retention time of 3.1 min. FTIR (ATR), vmax 2948, 2914, 2880, 2854, 1740, 1666 and 1613 cm$^{-1}$. $^1$H NMR (300 MHz, CDCl$_3$): δ 0.785 (d, 3H, J=7.2 Hz, C7α-CH$_3$), 0.895 (t, 3H, J=16.9 Hz, hexyl-CH$_3$), 0.956 (s, 3H, C18-CH$_3$), 1.062 (d, 3H, J=7.8 Hz, C11β-CH$_3$), 4.114 (t, 2H, J=6.9 Hz, hexyl-OCH$_2$—), 4.476 (dd, 1H, J=9.3 Hz, J2=7.2 Hz, C17α-CH) and 5.850 (s, 1H, C4-CH=) ppm. $^{13}$C NMR (300 MHz, CDCl$_3$): δ 12.884 (C7-CH$_3$), 13.991 (hexyl-CH$_3$), 15.215 (C18), 17.121 (C11-CH$_3$), 22.537, 22.648, 25.382, 26.428, 27.201, 28.430, 28.663, 30.755, 31.434, B6.649, 36.796, 38.734, 42.727, 43.284, 44.644, 45.763, 47.694, 68.065 (hexyl-OCH$_2$—), 87.087 (C17), 126.585 (C4), 155.402 (OC(=O)—), 165.537 (C5) and 199.423 (C3) ppm: MS (El) m/z (relative intensity): 430 (M+, 15), 302 (18), 284 (83), 173 (100), 159 (38), and 147 (44). Anal. Calcd. for C$_{27}$H$_{42}$O$_4$: C, 75.32; H, 9.83. Found: C, 75.47; H, 9.86.

17β-Decyloxycarbonyloxy-7α,11β-dimethylestr-4-en-3-one (2c, CDB-4719); Following the same procedure used to synthesize compound 2a, dimethandrolone (1, 1.0 g, 3.31 mmol) in dry CH$_2$Cl$_2$ (50 mL) was reacted with decyl chloroformate (2 mL, 8.66 mmol) in the presence of pyridine (1 mL, 12.4 mmol). Purification by flash chromatography using 1% acetone in CH$_2$Cl$_2$ followed by crystallization from hot hexanes gave 1.2 g of the pure product 2c in 74.6% yield; m.p. 66-68° C. Analysis by HPLC on NovaPak C-18 column, Waters Assoc., eluted with 100% CH$_3$CN at a flow rate of 1 mL/min and at λ=240 nm indicated compound 2c to be >99% pure with a retention time of 6.62 min. FTIR (ATR), vmax 2954, 2918, 2849, 1743, 1666 and 1613 cm$^{-1}$. $^1$H NMR (300 MHz, CDCl$_3$): δ 0.784<d, 3H, J=6.6 Hz, C7α-CH$_3$), 0.880 (t, J=6.6 Hz, 3H, decyl-CH$_3$), 0.955 (s, 3H, C18-CH$_3$), 1.062 (d, 3H, J=7.5 Hz, C11β-CH$_3$), 4.110 (t, 2H, J=6.9 Hz, decyl-OCH$_2$—), 4.473 (dd, J=9 Hz, J2=7.2 Hz, C17α-CH), and 5.848 (s, 11H, C4-CH=) ppm. $^{13}$C NMR (300 MHz, CDCl$_3$) δ 12.904 (C7-CH$_3$), 14.130 (decyl-CH$_3$), 15.237 (C18), 17.116 (C11-CH$_3$), 22.654, 22.689, 25.710, 26.434, 27.204, 28.443, 28.695, 29.252, 29.312, 29.500, 30.759, 31.906, 36.653, 36.814, 38.725, 42.708, 43.270, 44.640, 45.768, 47.704, 68.090 (decyl-OCH$_2$—), 87.107 (C17), 126.569 (C4), 155.410 (OC=O), 165.589 (C5) and 199.475 (C3) ppm. MS (El) m/z (relative intensity): 486 (M+, 34), 284 (87), 175 (100), and 147 (52). Anal. Calcd. for C$_{31}$H$_{50}$O$_4$·¼C$_6$H$_{14}$: C, 76.80; H, 10.61. Found: C, 77.02; H, 10.42.

17β-Dodecyloxycarbonyloxy-7α,11β-dimethylestr-4-en-3-one (2d, CDB-4730): Following the same procedure used in the synthesis of compound 2a, dimethandrolone (1, 1.0 g, 3.31 mmol) in CH$_2$Cl$_2$ (50 mL) was reacted with dodecyl chloroformate (2 mL, 7.4 mmol) in the presence of pyridine (1 mL, 12.4 mmol) to give 2.1 g of the crude product 2d. Purification by Flash chromatography (1% acetone in CH$_2$Cl$_2$) followed by crystallization from hot hexanes gave 1.3 g of the pure product 2d in 76% yield: m.p.=52.7-53.7° C. Analysis by HPLC on NovaPak C-18 column, Waters Assoc. eluted with 100% CH$_3$CN at a flow rate of 1 mL/min and at λ=240 nm indicated compound 2d to be >99% pure with a retention time of 8.65 min. FTIR (ATR), vmax 2953, 2920, 2851, 1743, 1668 and 1615 cm$^{-1}$.

$^1$HNMR (300 MHz, CDCl$_3$): δ 0.785 (d, 3H, J=7.2 Hz, C7α-CH$_3$), 0.882 (t, J=6.8 Hz, 3H, dodecyl-CH$_3$), 0.956 (s, 3H, C18-CH$_3$), 1.062 (d, 3H, J=7.5 Hz, C11β-CH$_3$), 4.110 (t, 2H, J=7.1 Hz, decyl-OCH$_2$—), 4.473 (dd, J=9 Hz, J2=7.4 Hz, C17α-CH), and 5.848 (s, 1H, C4-CH=) ppm. $^{13}$C NMR (300 MHz, CDCl$_3$): δ 12.870 (C7-CH$_3$), 14.122 (decyl-CH$_3$), 15.204 (C18), 17.104 (C11-CH$_3$), 22.657, 22.694, 25.726, 26.438, 27.212, 28.471, 28.713, 29.246, 29.356, 29.498, 29.549, 29.627, 30.766, 31.932, 36.671, 36.837, 38.757, 42.745, 43.276, 44.662, 45.767, 47.729, 68.078 (dodecyl-OCH$_2$—), 87.111 (C17), 126.602 (C4), 155.411 (OC—O), 165.477 (C5), and 199.477 (C3) ppm. MS (El) m/z (relative intensity): 514 (M$^+$, 50), 284.2 (81), 175.1 (100), and 57.0 (75). Anal. Calcd. for C$_{33}$H$_{54}$O$_4$: C, 77.04; H, 10.51. Found: C, 77.15; H, 10.54.

Figure 2:
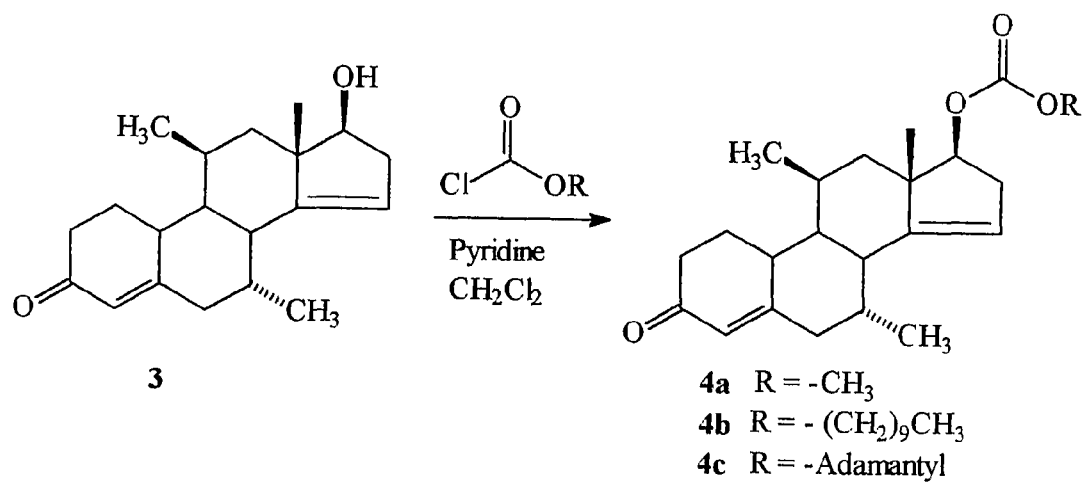
FIG. 2 depicts a reaction scheme to prepare dimethandrolone carbonates 4a-4-c in accordance with an embodiment of the invention. Compound 3 is $\Delta^{14}$-dimethandrolone.

The synthesis of Δ$^{14}$-dimethandrolone (3 or 7α,11β-dimethylestra-4,14-dien-3-one) has been described in U.S. Patent Publication No. 20030130243 A1. The syntheses of 17β-methyl, 17β-decyl and 17β-adamantyl carbonates of Δ$^{14}$-Dimethandrolone were carried out following the procedure in a manner similar to those of dimethandrolone 17-carbonates as described above. See also FIG. 2.

17β-Methoxycarbonyloxy-7α,11β-dimethylestra-4,14-dien-3-one (4a, CDB-4748): A solution of Δ$^{14}$-dimethandrolone (3, 150 mg, 0.50 mmol) in CH$_2$Cl$_2$ (7 mL) and pyridine (0.2 mL) was cooled to 0° C. in an ice bath and treated with methyl chloroformate (0.096 mL, 1.25 mmol). The solution was allowed to warm to room temperature and stirred for 5 hr. The reaction mixture was poured into cold water and extracted with dichloromethane. The dichloromethane extracts were washed with water, combined, and dried over Na$_2$SO$_4$. Evaporation of the solvent gave 182 mg of an oil. The material was chromatographed using 5% acetone in CH$_2$Cl$_2$ to yield 138 mg of 4a in 77% yield as a stable foam. The starting material 3 (35 mg) was recovered in 23% yield. Attempts for recrystallization of 4a from a variety of solvent systems were failed to give a solid. FTIR (ATR), vmax 2954, 1742, 1667, 1618, and 1261 cm$^{-1}$. $^1$H NMR (300 MHz, CDCl$_3$) δ 0.849 (d, 3H, J=7.2 Hz, C7α-CH$_3$), 1.113 (s, 3H, C18-CH$_3$), 1.119 (d, J=7.2 Hz, C11α-CH$_3$), 3.793 (s, 3H, —OCH$_3$), 4.780 (t, 1H, J=7.8 Hz, C17α-H), 5.166 (br s 1H, C15-H), and 5.876 (s, 1H, C4-CH=) ppm. MS (EI) m/z (relative intensity): 358 (M$^+$, 3.1), 282 (100), 190 (22.1), 173 (41.3), 157 (28.1) and 147 (48.8).

17β-Decyloxycarbonyloxy-7α,11β-dimethylestra-4,14-dien-3-one (4b, CDB-4749): Following the same procedure used to synthesize 4a, A4-Dimethandrolone (3, 150 mg, 0.50 mmol) in CH$_2$Cl$_2$ (7 mL) was reacted with decyl chloroformate (0.290 mL, 1.25 mmol) in the presence of pyridine (0.20 mL). Following work up and chromatography using 2% acetone in CH$_2$Cl$_2$, 246.3 mg of 4b was obtained as a clear oil which resisted efforts at recrystallization from a variety of solvents. FTIR (ATR), vmax 2922, 2853, 1740, 1671, 1618, 1254 and 977 cm−1. H$^1$ NMR (300 MHz, CDCl$_3$) δ 0.849 (d, 3H, J=7.2 Hz, C7α-CH3), 0.882 (t, 3H, J=8.0 Hz, —O(CH$_2$)$_9$CH$_3$), 1.115 (s, 3H, C18-CH$_3$), 1.117 (d, J=7.2 Hz, C11β-CH$_3$), 4.129 (t, J=8.0 Hz, —OCH$_2$(CH$_2$)$_8$CH$_3$) 4.780 (t, 1H, J=7.8 Hz, C17α-H), 5.166 (br s 1H, C15-H), and 5.876 (s, 1H, C4-CH=) ppm. MS (EI) m/z (relative intensity): 484 (M+, 2.5), 282 (100), 190 (12.5), 172 (31.9), 147 (46.9), and 145 (21.9).

17β-Adamantyloxycarbonyloxy-7α,11-dimethylestra-4,14-dien-3-one (4c, CDB-4650): A pyridine (35 mL) solution of 3 (280 mg, 0.93 mmol) was treated with adamantyl fluoroformate (740 mg, 3.73 mmol) and the solution was heated at reflux for 18 hours. The solution was chilled in an ice bath and diluted with cold water. The aqueous mixture was extracted with ethyl acetate (3×). The ethyl acetate extracts were washed with water and brine, combined, and dried over sodium sulfate. Evaporation of the solvent gave 970 mg of a semi-solid. The material was chromatographed using 2% acetone/dichloromethane) to yield 330 mg of 4c as a stable foam. The material was dissolved in ethanol (ca. 4 mL) and added dropwise to cold water (ca. 40 mL) while stirring vigorously. The resulting solid was filtered, washed with water, and dried in vacuo to yield 303 mg of 4c as a white powder: m.p.=97-100° C. NMR (CDCl$_3$) δ 0.847 (d, 3H, J=7 Hz, C7α-Me), 1.100 (s, 3H, C18-Me), 1.116 (d, 3H, J=7 Hz, C11β-Me), 4.730 (t, 11H, J=8 Hz, C17α-H), 5.150 (br. s, 11H, C15-C H=), 5.827 (s, 1H, C4-CH=) ppm. FTIR (ATR): 2908, 2851, 1723, 1670, 1610, 1238, 1041 cm$^{-1}$. MS (EI) m/z (relative intensity): 478 (M$^+$), 300, 282 (base), 190, 172, 147, 135.

Many of the 11β-substituted 19-nortestosterone such as methyl, ethyl, chloro and fluoro are known in U.S. Pat. Nos. 3,983,144; 3,325,520; 3,652,606; 4,292,251 and Steroids, 30, 481-510 (1977).

Figure 3:
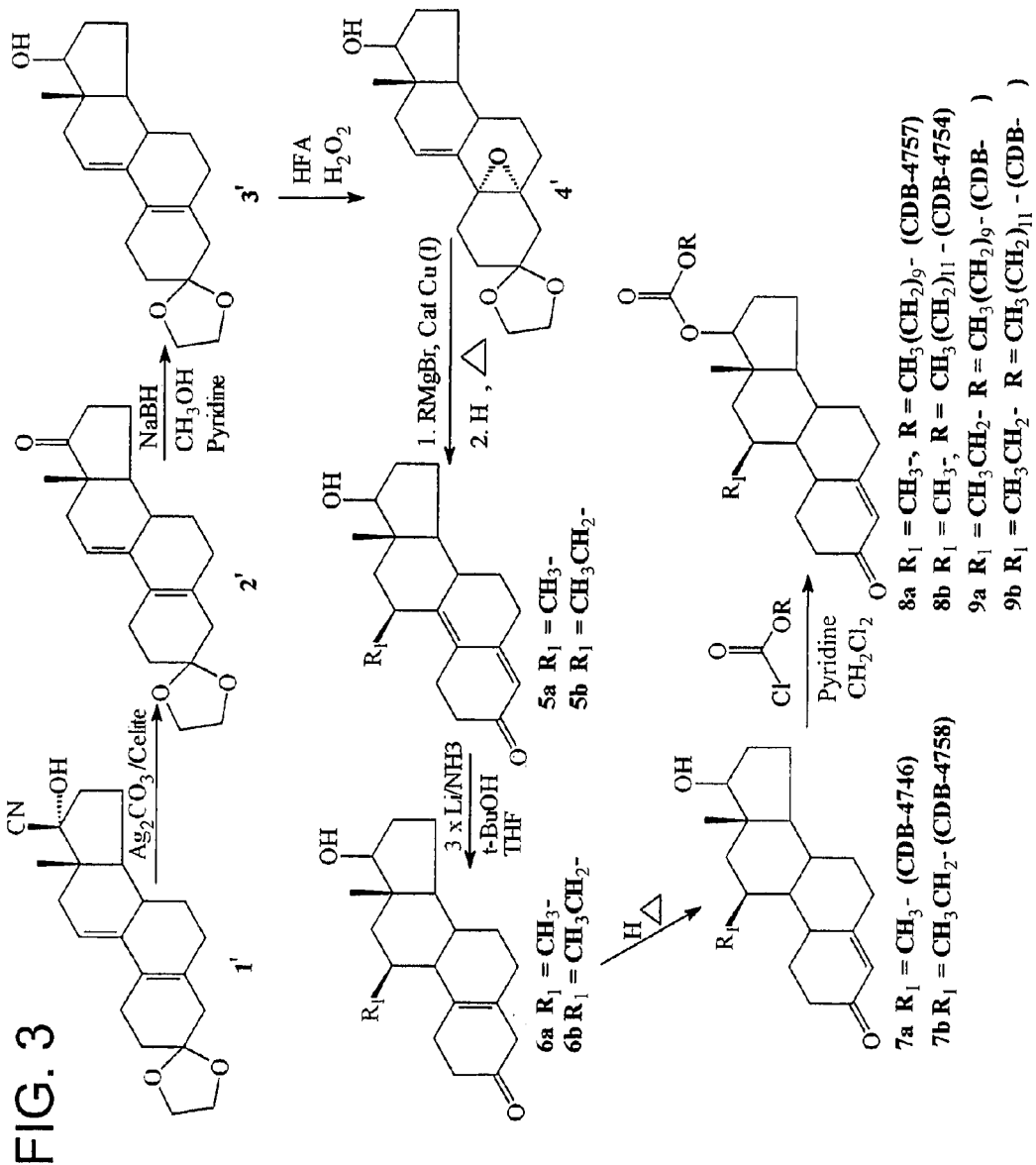
FIG. 3 depicts a reaction scheme to prepare nandrolone carbonates 8a-8b and 9a-9b in accordance with an embodiment of the invention.
Figure 4:
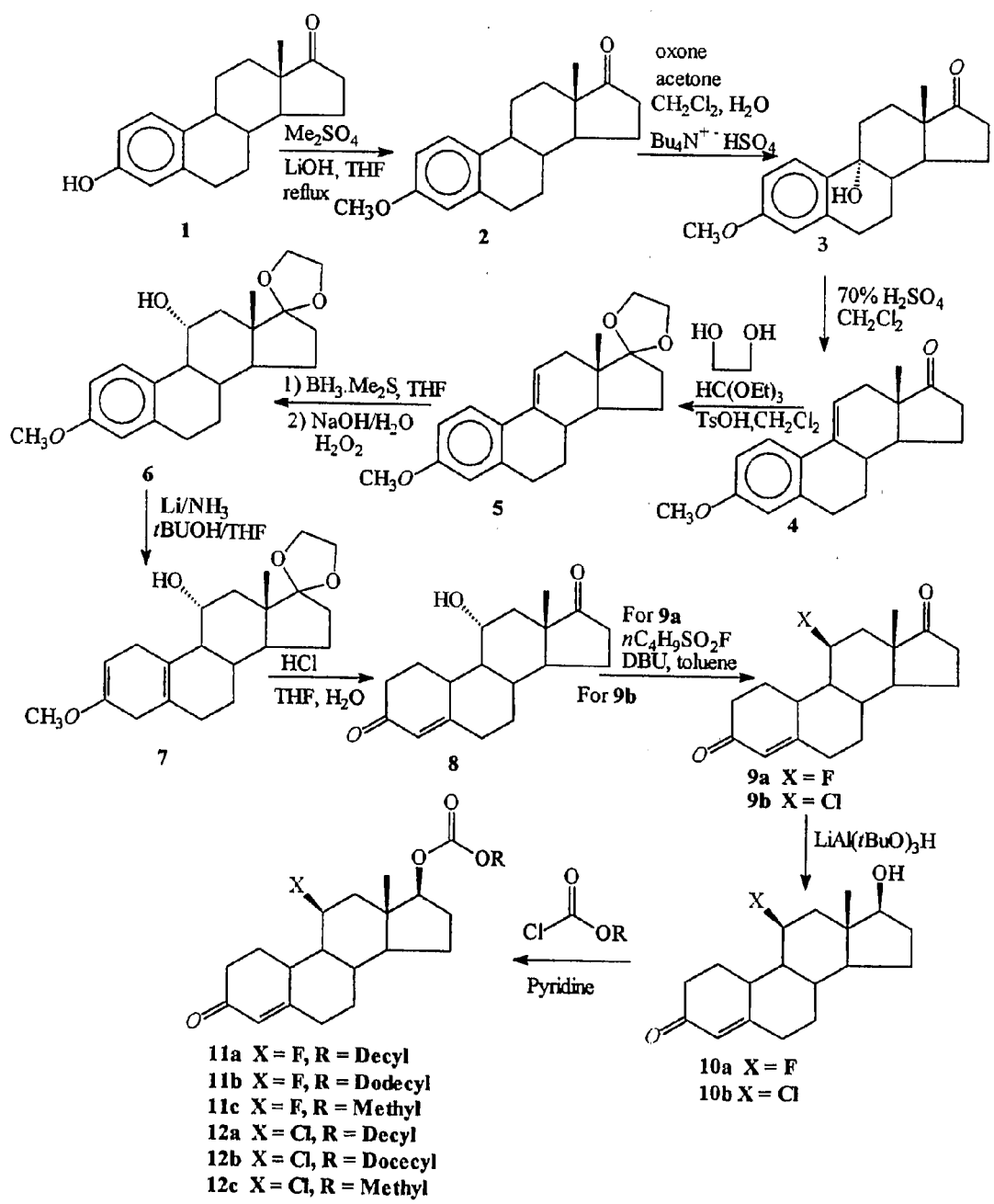
FIG. 4 depicts a reaction scheme to prepare nandrolone carbonates 11a-11e and 12a-12c in accordance with an embodiment of the invention.

11β-Methyl-17β-dodecyloxycarbonyloxyestr-4-en-3-one (8b), CDB-4754) (FIG. 3): 11β-Methyl 17β-hydroxyestra-4,9-diene (5a) was prepared in a manner similar to the procedure described in Muddana et al., *J. Med. Chem.*, 47, 4985-4988 (2004) for the preparation of the 11β-ethyl 17β-hydroxyestra-4,9-diene (5b).

11β-Alkyl-Δ$^9$-19-Nor-testerone derivatives: High-Affinity ligands and potent partial agonists of the androgen receptor. (1) 11β-Methyl-17β-hydroxyestr-4-en-3-one (7α, CDB-4746, FIG. 3).

3,3-Ethylenedioxy-5α,10α-epoxy-17β-hydroxyestr-9(11)-ene (4'): 30% hydrogen peroxide (6.7 mL, 65.1 mmol) was added to an ice-cold CH$_2$Cl$_2$ (70 mL) solution of hexafluoro-acetone trihydrate (13.15 g, 65.1 mmol). Disodium hydrogen phosphate (3.9 g, 27.47 mmol) was added and the mixture was stirred at 0° C. for 2 hr. A CH$_2$Cl$_2$ (70 mL) of 3,3-Ethylenedioxy-17β-hydroxyestra-5(10), 9(11)-diene (3', 6.85 g, 21.69 mmol) was added and the mixture was stirred at 0-4° C. overnight. The reaction was quenched through the addition of 10% sodium sulfate solution (100 mL). The aqueous mixture was extracted with CH$_2$Cl$_2$. The CH$_2$Cl$_2$ extracts were washed with H$_2$O and brine, combined, and dried over Na$_2$SO$_4$. Evaporation of the solvent gave 7.75 g of the epoxides as a stable foam in quantitative yield. NMR analysis of the material showed it to be approximately a 5:1 mixture of 5α,10α-/5β,10β-epoxides. The material was used without further purification in the following reaction. NMR (300 MHz, CDCl$_3$) δ 0.744 (s, 3H, C18-Me), 3.747 (t, 1H, J=7 Hz, C17α-H), 3.928 (m, 4H, 3-ketal), 5.836 (m, C11β-H of 5β,10α-epoxide) and 6.038 (m, C11α-H of 5α,10α-epoxide).

11β-Methyl-17β-hydroxyestra-4,9-diene (5a): A solution of methyl-magnesium bromide (1.4 M THF/toluene) was added to 95 mL of THF and 1.9 g of copper (I) chloride was added. After stirring at room temperature for 2 hr a THF solution of the 5α,10α-epoxide (=3,3-ethylenedioxy-5α,10α-epoxy-17β-hydroxyestra-9(11)-ene (10 g, 0.035 mol) was added dropwise over 5 min. The mixture was stirred at room temperature for 3 hr. The mixture was diluted with saturated ammonium chloride solution and air bubbled through the mixture for 2 hr to oxidize Cu (I) to Cu (II). The aqueous mixture was extracted with ether (3×). The ether extracts were washed with H$_2$O and brine, combined, and dried over Na$_2$SO$_4$. Evaporation of the solvent gave 9.83 g of yellow solid.

This solid was dissolved in methanol (400 mL) and 10% HCl solution (40 mL) was added. The solution was heated to reflux for 3 hr. The solvent was evaporated in vacuo and the residue was diluted with water, extracted with ether (3×). The ether extracts were washed with H$_2$O and brine, combined, and dried over Na$_2$SO$_4$. Evaporation of solvent gave 9.83 g of yellow solid.

The solid was dissolved in methanol (400 mL) and 40 mL of 10% of HCl was added. The solution was heated to reflux for 3 hr. The solvent was evaporated in vacuo and the residue was treated with saturated sodium bicarbonate solution. The aqueous mixture was extracted with CH$_2$Cl$_2$. The CH$_2$Cl$_2$ extracts were washed with H$_2$O and brine, combined, and dried over Na$_2$SO$_4$. Evaporation of the solvent gave 8.3 g of the crude 5a as a stable foam in 82% yield. The crude material was chromatographed by eluting with 11% acetone/CH$_2$Cl$_2$ to afford 6.1 g of 5a. Recrystallization of the solid 5a from acetone/hexane gave 4.03 g of a yellow crystalline solid in three crops in 47% yield: m.p.=194-195° C. IR (ATR): vmax 3394, 2939, 1641 and 1576 cm$^{-1}$. NMR (300 MHz, CDCl$_3$): δ 0.979 (s, 3H, C18-CH$_3$), 1.170 (d, 3H, C11-CH$_3$), 3.642 (t, 1H, C17β-H) ppm.

11β-Methyl 17β-hydroxyestr-5(10)-en-3-one (6a): Under an argon atmosphere, lithium wire (270 mg, 38.9 mmol), cut into small pieces, was added to anhydrous ammonia (200 mL) and stirred at reflux for 2 hr. The lithium/ammonia mixture was chilled to −78° C. and a THF solution of the dienone (5a, 4.03 g, 14.07 mmol) containing t-butanol (1.24 mL), was added over 15 min. The mixture was stirred at −78° C. for 15 min before excess of lithium was destroyed with isoprene (1.5 mL). The reaction was quenched by means of the addition of solid ammonium chloride (16 g, 296.3 mmol). Ammonia was allowed to evaporate under a constant stream of nitrogen. The THF layer was washed with H$_2$O and brine. The aqueous washes were extracted with ether (2×200 mL). the combined organic extracts were dried over Na$_2$SO$_4$ and evaporation of the solvent gave 4.25 g of 6a as a white solid in 100% yield. NMR (300 MHz, CDCl$_3$): δ 0.889 (s, 3H, C18-7CH$_3$), 0.916 (d, 3H, C11β-CH$_3$), and 3.655 (t, 1H, C17β-H) ppm.

11β-Methyl 17β-hydroxyestr-4-en-3-one (7α, CDB-4746)): The white solid (6a, 4.25 g, 14.73 mmol) was dissolved in methanol (400 mL) and 40% of 10% HCl was added. The solution was heated to reflux for 3 hr. The solvent was evaporated in vacuo and the residue was diluted with saturated sodium bicarbonate solution and extracted with CH$_2$Cl$_2$ (3×500 mL). The methylene chloride extracts were washed with H$_2$O and brine, combined, and dried over Na$_2$SO$_4$. Evaporation of solvent gave 4.20 g of a yellow crystalline solid in 99% yield. The crude material was recrystallized from acetone/hexane to give 1.49 g of solid (7α, CDB-4746) in two crops in 35% yield. m.p.=160-161° C. Analysis by a reverse phase HPLC on a Waters Associate NovaPak C$_{18}$ column eluted with 50% aqueous CH$_3$CN, at a flow rate of 1 mL/min and at λ=240 nm indicated 100% purity of 7a with retention time, $t_R$=3.2 min. FTIR (ATR): vmax 3404, 2939, 2898, 1637, and 1435 cm$^{-1}$. NMR (300 MHz, CDCl$_3$) δ 0.887 (s, 3H, C18-CH$_3$), 1.008 (d, 3H, C11β-CH$_3$), 3.615 (t, 1H, C17_-H), and 5.851 (s, 1H, C4-CH=) ppm. MS (EI) m/z (relative intensity): 288 (M$^+$, 100), 270 (28), 246

(25), 229 (25), 179 (22), 161 (28), 133 (29), 109 (50) and 90 (22). Anal. Calcd. for $C_{19}H_{28}O_2$: C, 79.05, H, 9.70. Found: C, 79.05, H, 9.78.

11β-Methyl-17-dodecyloxycarbonyloxy estr-4-en-3-one (8b, CDB-4754). Dodecyl chloroformate (1.23 g, 4.94 mmol) was added dropwise to a solution of 7a (950 mg, 3.39 mmol) in $CH_2Cl_2$ (50 mL) and pyridine (1.30 g, 5 eq) chilled at 0° C. After addition, and removal of ice bath it was allowed to stir at room temperature for 4 hr. The reaction was monitored by Thin Layer Chromatography (TLC) (2% acetone/$CH_2Cl_2$). The organic layer was washed with $H_2O$ and brine, combined, and dried over $Na_2SO_4$. Evaporation of the solvent gave 2.67 g of solid. This material was chromatographed over silica (2% acetone/$CH_2Cl_2$) and recrystallized twice from pentane, recovering 1.11 g of a fine white crystalline powder (8b, CDB-4754) in 43% yield. m.p.=54.7-55.4° C. Analysis by a reverse phase HPLC on a Waters Associate NovaPak $C_{18}$ column eluted with 50% $H_2O$ in $CH_3CN$, at a flow rate of 1 mL/min and at λ=240 nm indicated 100% purity of 8b with retention time, $t_R$=12.13 min. FTIR (ATR): vmax 2899, 2848, 1727, 1616, and 1253 $cm^{-1}$. NMR (300 MHz, $CDCl_3$) δ 0.881 (s, 3H, C18-$CH_3$), 1.052 (d, 3H, C11β-$CH_3$), 4.109 (t, 1H, C17β-H), and 5.848 (s, 1H, C4-C H=) ppm. MS (EI) m/z (relative intensity): 500.52 ($M^+$, 57), 271 (44), 270 (48), 161(100), 160 (70), 147 (41), 119 (34), and 110 (65). Anal. Calcd. for $C_{32}H_{52}O_4$: C, 76.68, H, 10.38. Found: C, 76.44, H, 10.37.

11β-Methyl-17β-decyloxycarbonyloxyestr-4-en-3-one (8a, CDB-4757): Decyl chloroformate (7.6 mL, 2 eq) was added dropwise with a syringe to a solution of 7a (5.0 g, 17.33 mmol) in $CH_2Cl_2$ (250 mL) and pyridine (6.9 g, 5 eq) chilled at −4° C. After completion of addition of decyl chloroformate, the ice bath was removed and the reaction mixture was stirred for 5 hr at room temperature. The reaction was monitored by TLC (3% acetone/$CH_2Cl_2$). The reaction mixture was poured into cold distilled $H_2O$; and the lower organic phase was washed with $H_2O$ and brine. All aqueous washes were extracted twice with $CH_2Cl_2$. The combined $CH_2Cl_2$ were dried over anhydrous $Na_2SO_4$. Evaporation of the solvent gave 8.9 g of a white solid. The crude white solid was recrystallized from pentane to afford 3.9 g of a white crystalline powder in 47.6% yield. m.p.=48.9 −49.3° C. Analysis by a reverse phase HPLC on a Waters Associate NovaPak $C_{18}$ column eluted with 100% $CH_3CN$, at a flow rate of 1 mL/min and at λ=240 nm indicated 100% purity of (8a, CDB-4757) with retention time, $t_R$=6.99 min. FTIR (ATR): vmax 2919, 2848, 1727, 1621, 1379, 1253 and 960 $cm^{-1}$. NMR (300 MHz, $CDCl_3$): δ0.880 (s, 3H, C18-$CH_3$), 1.052 (d, 3H, C11β-$CH_3$), 4.108 (t, 1H, C17β-H), and 5.847 (s, 1H, C4-C H=) ppm. MS (EI) m/z (relative intensity): 472 ($M^+$, 27), 270 (41), 161 (100), 145 (36), 119 (31), and 110 (21). Anal. Calcd for $C_{30}H_{48}O_4$: C, 76.16, H, 10.15. Found: C, 76.05, H, 10.29.

11β-Ethyl-17β-dodecyloxycarbonyloxyestr-4-en-3-one (9b, CDB-4722) was prepared from 7b. (1) 11β-Ethyl-17β-hydroxyestr-4-en-3-one (7b, CDB-4758, FIG. 3) was prepared from 5b as follows: 3,3-Ethylenedioxy-5α,10α-epoxy-17β-hydroxyestr-9(11)-ene: 30% hydrogen peroxide (6.7 mL, 65.1 mmol) was added to an ice-cold $CH_2Cl_2$ (70 mL) solution of hexafluoro-acetone trihydrate (13.15 g, 65.1 mmol). Disodium hydrogen phosphate (2.8 g, 19.74 mmol) was added and the mixture was stirred at 0° C. for 2 hr. A $CH_2Cl_2$ (70 mL) of 3,3-ethylenedioxy-17β-hydroxyestra-5 (10), 9(11)-diene (6.85 g, 21.69 mmol) was added and the mixture was stirred at 0-4° C. overnight. The reaction was quenched through the addition of 10% sodium sulfate solution (100 mL). The aqueous mixture was extracted with $CH_2Cl_2$. The $CH_2Cl_2$ extracts were washed with $H_2O$ and brine, combined, and dried over $Na_2SO_4$. Evaporation of the solvent gave 7.75 g of the epoxides as a stable foam in quantitative yield. NMR analysis of the material showed it to be approximately a 5:1 mixture of 5α,10α-/5β,10β-epoxides. The material was used without further purification in the following reaction. NMR (300 MHz, $CDCl_3$) δ 0.744 (s, 3H, C18-Me), 3.747 (t, 1H, J=7 Hz, C17α-H), 3.928 (m, 4H, 3-ketal), 5.836 (m, C11β-H of 5β,10β-epoxide) and 6.038 (m, C11α-H of 5α,10β-epoxide).

11β-Ethyl-17β-hydroxyestra-4,9-dien-3-one (5b): Ethyl magnesium bromide (1.0 M/THF, 19.5 mL, 19.5 mmol) was chilled to 0° C. and diluted dry ether (19.5 mL). With stirring, copper chloride (193.6 mg. 1.95 mmol) was added over 2 hr and the mixture was allowed to stir for 45 min. A THF (50 mL) of the epoxide (1.0 g, 3.01 mmol) prepared according to the procedure described above was added over 2 hr to the mixture. The reaction mixture was stirred for 3 hr at 0° C. and then carefully quenched through the addition of a saturated ammonium chloride solution (100 mL). While stirring, air was drawn through the mixture to oxidize Cu(I) to Cu(II). The mixture was extracted with ether. The ether extracts were washed with $H_2O$ and brine, combined, and dried over $Na_2SO_4$. Evaporation of the solvent gave 1.24 g of a stable foam. The above product from two identical reactions (2.58 g) was dissolved in methanol (200 mL) and 10% HCl solution (20 mL) was added. The solution was stirred overnight at room temperature. The methanol was evaporated in vacuo and the residue was diluted with water. The aqueous mixture was extracted with $CH_2Cl_2$. The $CH_2Cl_2$ extracts were washed with $H_2O$ and brine, combined, and dried over $Na_2SO_4$. Evaporation of the solvent gave 1.73 g. The crude material was chromatographed eluting with 12% acetone/to afford 660 mg of the dien-one 5b as a stable foam in 71% yield. Repeated efforts at crystallization of this material from a variety of solvents were unsuccessful. The material was homogeneous by TLC and NMR analysis showed it to be only one epimer. NMR (300 MHz, $CDCl_3$): δ 0.931 (t, 3H, J=7.2 Hz, —$CH_2$-$CH_3$), 0.963 (s, 3H, C18-$CH_3$), 3.645 (t, 1H, J=7 Hz, C17α-H), and 5.683 (s, 1H, C4-CH=) ppm.

11β-Ethyl-17β-hydroxyestr-4-en-3-one (7b, CDB-4758) (2): Lithium wire (45.74 mg, 6.59 mmol), cut into small pieces, was added to anhydrous ammonia (ca. 20 mL). The mixture was stirred at −35° C. for 20 min. After chilling, the reaction mixture to −78° C., a THF (20 mL/t-butanol (0.21 mL, 2.22 mmol) solution of the dien-one (5b, 660 mg, 2.22 mmol) was added dropwise over 10 min. After stirring for 15 min, excess lithium was destroyed through the addition of isoprene (1.0 mL), followed by the addition of ammonium chloride (2.64 g). The ammonia was evaporated under as stream of nitrogen. The residue was diluted with phosphate buffer (0.1 M, pH=7.0, 50 mL). The aqueous mixture was extracted with ether. The ether extracts were washed with $H_2O$ and brine, combined, and dried over $Na_2SO_4$. Evaporation of the solvent gave 850 mg. The crude material above was dissolved in methanol (125 mL) and 10% HCl solution (12.5 mL) was added. The solution was heated at reflux for 4 hr. The solvent was evaporated in vacuo and the residue was diluted with $H_2O$. The aqueous mixture was extracted with $CH_2Cl_2$. The $CH_2Cl_2$ extracts were washed with $H_2O$ and brine, combined, and dried over $Na_2SO_4$. Evaporation of the solvent gave 720 mg of a stable foam. The material was chromatographed using 3% MeOH/$CH_2Cl_2$ to give 400 mg in 60% yield. This material was recrystallized from acetone/hexanes to give 182 mg of pure 7b as a white crystalline powder in 27% yield. m.p.=147-148° C. Analysis by a reverse phase HPLC on a Waters Associate NovaPak $C_{18}$ column eluted with 50% aq. $CH_3CN$, at a flow rate of 1.0 mL/min and at λ=240 nm indicated 98% purity of 8a (CDB-4757) with retention time, $t_R$=4.62 min. FTIR (ATR): vmax 3433, 2958, 2858, 1651, 1613, 1447, 1262, 1212, 1070, 974 and 889 cm$^{-1}$. $^1$H NMR (300 MHz, CDCl$_3$) δ 0.888 (s, 3H, C18-CH$_3$), 0.922 (t, 3H, J=7.2 Hz, C11β-CH$_2$CH$_3$), 3.627 (t, 1H, J=7 Hz, C17β-H), and 5.846 (s, 1H, C4-CH=) ppm. $^{13}$C NMR (CDCl$_3$) δ 12.741, 13.359, 20.645, 23.086, 25.947, 30.131, 35.265, 35.912, 37.415, 38.036, 42.849, 52.022, 53.595, 82.750, 124.200, 168.043, and 199.928 ppm. MS (EI) m/z (relative intensity): 302.6 (M$^+$), 284.6 (M$^+$ –18, 9), 193 (26), 175 (11), 147 (18), 133 (24), 123 (38), and 110 (100). Anal. Calcd. for C$_{20}$H$_{30}$O$_2$C, 79.46, H, 9.81. Found: C, 79.42, H, 10.00.

11β-Ethyl-17β-dodecyloxycarbonyloxyestr-4-en-3-one (9b, CDB-4722) was prepared as follows: Under nitrogen, a solution of 11β-ethylestr-4-en-17β-ol (7b, 0.1 g, 0.33 mmol) in dry CH$_2$Cl$_2$ (5 mL) was cooled to 0° C. in an ice bath. Pyridine (0.1 mL, 97.8 mg, 1.24 mmol) followed by dodecyl chloroformate (0.2 mL, 1.84 mg, 0.74 mmol) were added and the mixture stirred at 0° C. for 15 min and then allowed to warm to room temperature. The reaction was stirred at room temperature overnight, after which time, TLC (2% acetone in CH$_2$Cl$_2$) indicated a complete reaction. The mixture was diluted with additional CH$_2$Cl$_2$ (50 mL) and washed with water (1×), saturated sodium bicarbonate solution (1×), and water (1×). The organic fractions were filtered through anhydrous Na$_2$SO$_4$, combined and concentrated in vacuo to give 0.3 g residue as a clear oil. This crude material was purified by Flash chromatography (2% acetone in CH$_2$Cl$_2$) to give 0.16 g of a clear oil in 94% yield, which resisted crystallization.

Analysis by HPLC on Waters Assoc. NovaPak C-18 eluted with 100% CH$_3$CN at a flow rate of 1 mL/min and at λ=240 nm) indicated compound 9b to be 99% pure with a retention time ($t_R$) of 12.37 min. FTIR (ATR) vmax 2923, 2853, 1740, 1674 and 1526 cm$^-$.

$^1$H NMR (300 MHz, CDCl$_3$) δ 0.882 (t, 3H, J=6.8 Hz, dodecyl CH$_3$), 0.956 (s, 3H, C18-CH$_3$), 0.981 (t, 3H, J=7.4 Hz, C11β-CH$_2$CH$_3$), 4.119 (t, 2H, J=6.8 Hz, dodecyl-OCH$_2$—), 4.468 (dd, 1H, J1=9 Hz, J2=7.2 Hz, C17α-CH), and 5.858 (s, 1H, C4-CH=).

$^{13}$C NMR (75 MHz, CDCl$_3$) δ 12.818 (C11β-CH$_2$CH$_3$), 14.124 (dodecyl-CH$_3$), 14.344 (C18), 20.743, 22.681, 23.117, 25.693, 26.0690, 27.288, 28.680, 29.239, 29.339, 29.492, 29.555, 29.621, 31.410, 31.913, 35.019, 35.225, 36.243, 37.624, 37.959, 38.024, 42.675, 51.756, 53.446, 68.022 (dodecyl-OCH$_2$—), 87.134 (C17), 124.426 (C4), 155.361 (carbonate C=O), 167.444 (C5) and 199.652 (C3) ppm. Anal. Calc'd for C$_{33}$H$_{54}$O$_4$: C, 77.04, H, 10.51.

EXAMPLE 2

This example demonstrates some of the biological activity of compounds in accordance with an embodiment of the invention. The androgenic activity was tested as follows (see, Hershberger et al., *Proc. Soc. Exptl. Biol. Med.*, 83: 175-180 (1953)). Immature (approximately 21 day old) male rats of the Sprague-Dawley strain were orchidectomized under METOFANE® anesthesia and randomly assigned to groups of ten animals for each dose level of test material and vehicle controls. Animals were maintained under standard conditions of housing and had free access to food and water. Illumination was controlled for 14-hour periods of light and 10 hours of darkness. Test compounds were dissolved in 10% ethanol/sesame oil and administered by gavage (oral) or subcutaneous injection daily for seven consecutive days starting on the day of surgery. Animals were sacrificed 24 hours after the last dose and the ventral prostate and seminal vesicles excised, cleaned of fat and connective tissue, blotted on moist filter paper and weighed to the nearest 0.1 mg. Ventral prostate weight was used as the endpoint because ventral prostate is the more sensitive organ to androgenic stimulation.

Statistical analysis was performed by conventional methods using a PROPHET data management system operating on SUN Microsystems OS 4.1.1 (see e.g., Bliss, Cl (1952) *The Statistics of Bioassay*, New York, Academic Press; Hollister, C (1988), *Nucleic Acids Research*, 16:1873-1875.

Duration of androgenic activity was determined as follows. Immature (22 days of age) male rats of the Sprague-Dawley CD strain were orchidectomized under METOFANE anesthesia and randomly assigned to groups of forty or more animals. Animals were maintained under standard conditions of housing and had free access to food and water. Illumination was controlled for 14-hour periods of light and 10 hours of darkness. Animals received a single subcutaneous injection of 0.6 mg of test material in aqueous suspending vehicle (ASV) and/or an oily vehicle (10% ethanol/sesame oil, sesame oil containing 5 mg/ml chlorobutanol as a preservative or ethyl oleate) on the day of surgery. Controls received vehicle alone. Testosterone enanthate in sesame oil was used as a standard. In cases where the test material was not solid at room temperature, i.e., a wax or oil, 10% ethanol/sesame oil or ethyl oleate was used as a vehicle. Five rats from each group were sacrificed at weekly or biweekly intervals and seminal vesicle and ventral prostate glands were excised, cleaned of adherent fat and connective tissue and weighed to the nearest 0.1 mg. Ventral prostate weight was used as the endpoint because it is the more sensitive organ to androgenic stimulation. Area under the curve (AUC) was calculated by the trapezoidal rule.

Serum levels of testosterone and CDB-1321 were determined as follows. Rats from a duration of androgenic activity study were exsanguinated at autopsy, serum prepared by allowing blood to clot at room temperature and the sample frozen for subsequent radioimmunoassay. A radioimmunoassay for the free alcohol, 7a, 11β-dimethyl-19-nortestosterone, was developed using antisera generated in rabbits against the 3-carboxymethyloxime-BSA conjugate and employing the corresponding histamine conjugate for iodination as tracer. The assay was validated for rat serum and exhibited high specificity for the free alcohol, CDB-1321.

Figure 5:
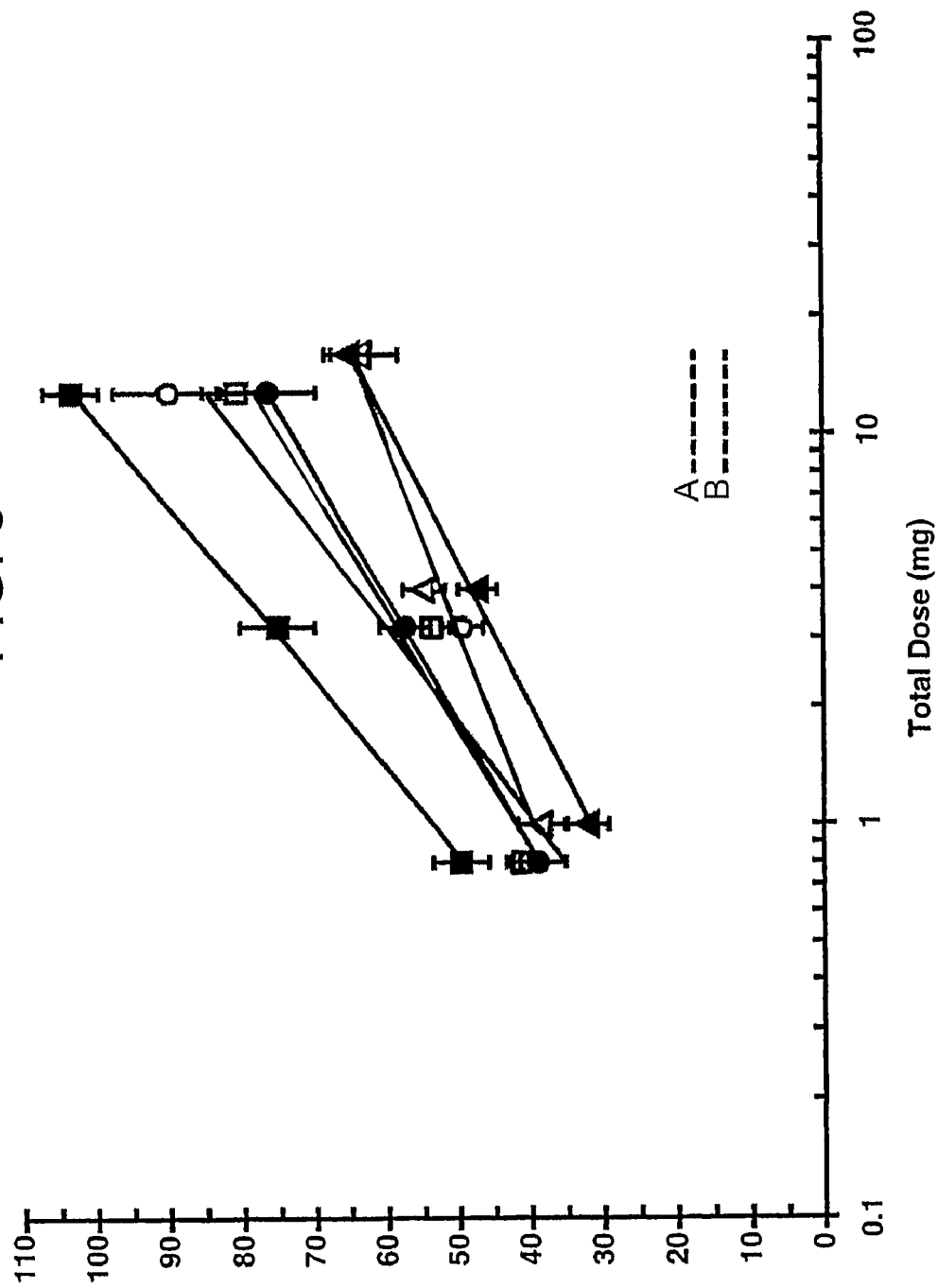
FIG. 5 depicts the androgenic activity; in a Hershberger test, of compounds CDB-4730 (2d, open circles), CDB-4731 (2b, open squares), CDB-4718 (2a, filled circles), and CDB-4719 (2c, filled squares) following an oral administration to castrate Sprague-Dawley male rats in 10% ethanol/sesame oil, in accordance with an embodiment of the invention. CDB-110B (methyltestosterone standard): open triangles, standard for CDB-4730 and CDB-4731 and filled triangles standard for CDB-4718 and CDB-4719. 'A' is vehicle control for CDB-4730 and 4731. 'B' is vehicle control for CDB-4718 and 4719.
Figure 6:
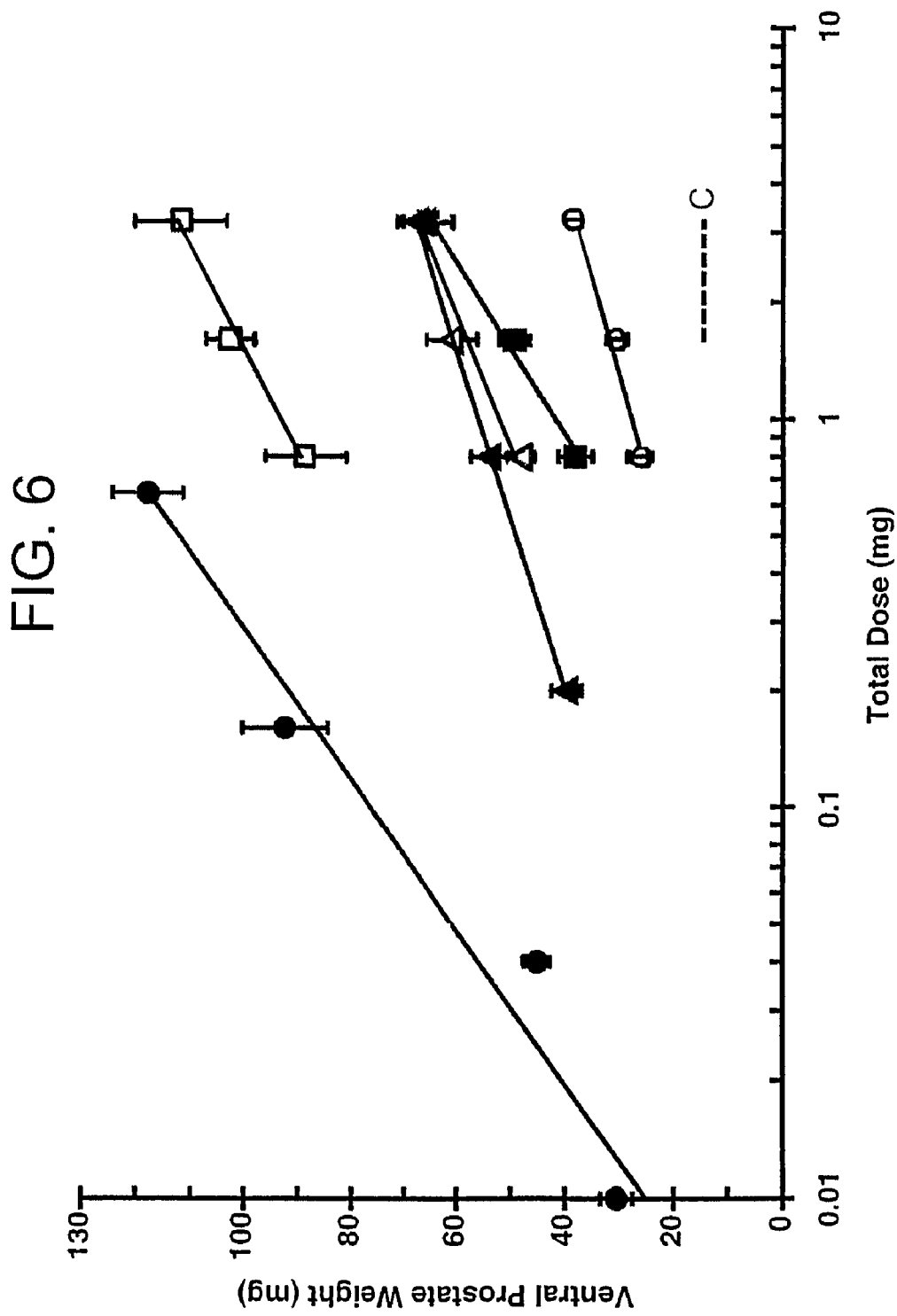
FIG. 6 depicts the androgenic activity, in a Hershberger test, of compounds CDB-4718 (2a, filled circles), CDB-4719 (2c, filled squares), CDB-4730 (2d, open circles), and CDB-4731 (2b, open squares) following a subcutaneous injection to castrate Sprague-Dawley male rats of the compounds in an aqueous suspending vehicle, in accordance with an embodiment of the invention. CDB-1111C (testosterone standard): filled triangles standard for CDB-4718, 4730, and 4731; and open triangles standard for CDB-4719. 'C' is mean vehicle control.

Results of the androgenic assays of CDB-4718 (2a), 4719 (2c), 4730 (2d), and 4731 (2b) are shown in FIGS. 5 and 6. Each data point represents the mean (n=10) and standard error of the mean (SEM) prostate weight for each dose level. The potency ratio and 95% confidence index are set forth below.

| CDB No. | ANDROGENIC ACTIVITY | |
|---|---|---|
| | Potency Ratio | 95% C.I. |
| 4718 | 2.609[1] | 1.554-4.381 |
| 4719 | 5.486-8.992[1,2] | — |
| 4730 | 0.97-3.82[1,2] | — |
| 4731 | 1.18-3.27[1,2] | — |
| 4718 vs. 4719 | 3.016 | 1.824-4.988 |

[1] CDB 110 (Methyl testosterone) = 1.000 assigned.
[2] Did not pass all significance test.

Fitted Lines:

| | |
|---|---|
| O CDB-4718: | Y = 31.31 log (x) + 41.95 |
| Δ CBD-4719: | Y = 44.41 log (x) + 53.7 |
| □ CBD-110B: | Y = 27.45 log (x) + 31.77 |

| | ANDROGENIC ACTIVITY | |
|---|---|---|
| CDB No. | Potency Ratio | 95% C.I. |
| 4718 | 10.4-47.5[1,2] | — |
| 4719 | 0.64 | 0.42-0.98 |
| 4730 | 0.05[1,2] | 0.03-0.11 |
| 4731 | 32.0[1,2] | 4.2-241.2 |

[1]CBD-111 (Testosterone) = 1.000 assigned
[2]Did not pass all significance tests.

CDB-4718, 7α,11β-Dimethyl-19-nortestosterone 17-methylcarbonate (2a), exhibited about two and one-half times the oral activity of the standard, methyltestosterone, but 10.4-47.5 times testosterone following subcutaneous injection in sesame oil vehicle. These findings were completely unexpected since testosterone and its esters are poorly active on oral administration. The potent activity following subcutaneous injection was also surprising given the short duration of action following a single subcutaneous injection in aqueous vehicle. The subcutaneous standard, testosterone, exhibited the expected activity. Similar findings were observed following both routes of administration using seminal vesicle weight as an endpoint.

CDB-4719, 7α,11β-dimethyl-19-nortestosterone 17-decylcarbonate (2c), exhibited five to nine times the oral activity of methyltestosterone but was no more potent than testosterone standard upon subcutaneous injection. On the other hand, it was far more potent than testosterone in the duration of activity test.

CDB-4730, 7α,11β-dimethyl-19-nortestosterone 17-dodecylcarbonate (2d), exhibited 0.97-3.82 times the oral activity of methyltestosterone standard but only 5% of the potency of the subcutaneous standard, testosterone. However, it was far more potent in the duration of androgenic activity test.

CDB-4731, 7α,11β-dimethyl-19-nortestosterone 17-hexylcarbonate (2b), exhibited 1.18-3.27 times the oral activity of methyltestosterone but 32 times the potency of the subcutaneous standard, testosterone.

The potent oral activity may be explained, in part, by the fact that the ester may be protected from degradation in the gastrointestinal tract and/or rapid metabolism by the liver. It is also possible that the lipophilic nature of some esters (particularly the decylcarbonate) permits absorption through the thoracic lymph thus avoiding direct entrance into the portal system and "first-pass" metabolism in the liver. The oral activity of these esters cannot be predicted but must be determined by direct in vivo bioassay. Within a certain range of carbon chain length, there is probably some correlation with lipophilicity.

The lack of potent subcutaneous activity of the decylcarbonate and dodecylcarbonate in the standard Hershberger test probably reflects the slow release (and possibly metabolism) of the drug from the injection site over the 7-day administration period. This is the very property that conveys long-acting activity upon parenteral administration in an aqueous vehicle.

Figure 7:
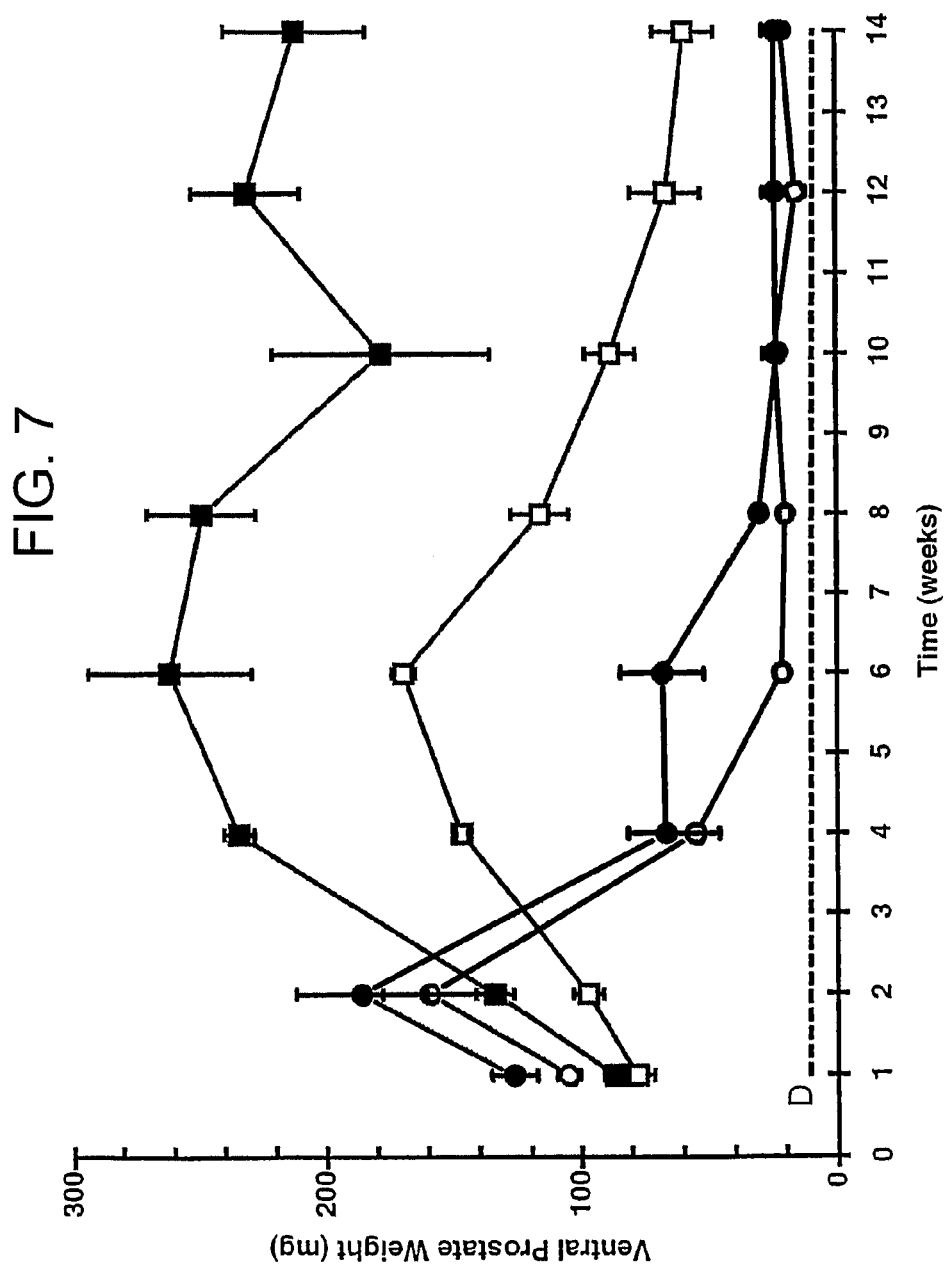
FIG. 7 depicts the duration of androgenic activity of CDB-4718 (2a, open circles, 0.6 mg; filled circles, 1.2 mg) and CDB-4719 (2c, open squares, 0.6 mg; filled squares, 1.2 mg) as a function time, following a single subcutaneous injection of the compounds to castrate Sprague-Dawley male rats. The AUC's (mg·week) were as follows: open circles, 581; filled circles, 789; open squares, 1417; and filled squares, 2764. 'D' is vehicle control, with an AUC of 126 mg·week.
Figure 8:
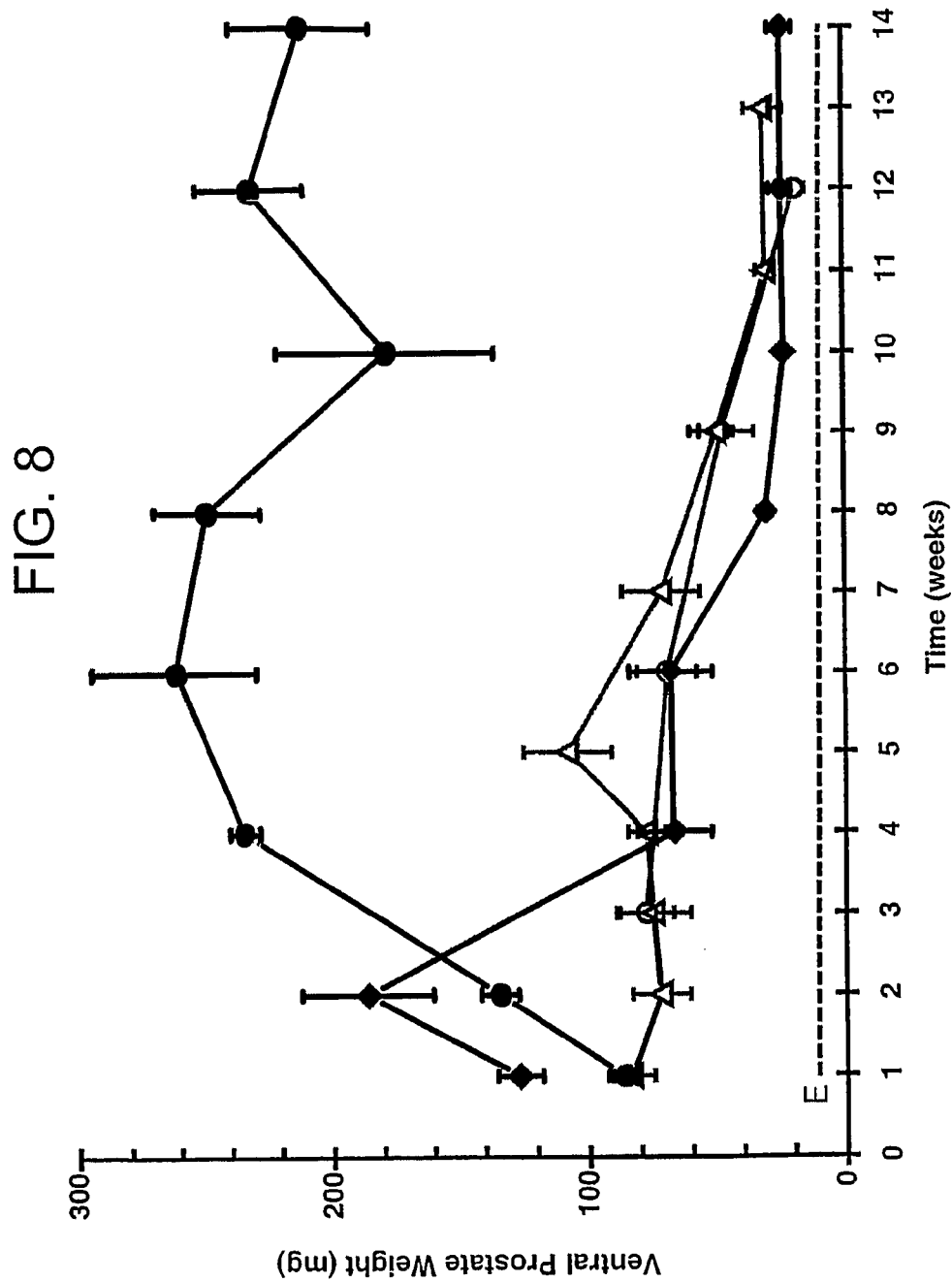
FIG. 8 depicts the duration of androgenic activity of CDB-4718 (2a, filled diamonds), CDB-4719 (2c, filled circles) following a single subcutaneous injection to castrate Sprague-Dawley male rats of 1.2 mg of the compounds in an aqueous suspending vehicle. CDB-3122E (testosterone undecanoate, open circles) and CDB-112 (testosterone enanthate in sesame oil, open triangles) were also tested at 1.2 mg and are shown for comparison. The AUC's (mg·week) were as follows: open circles, 494; open triangles, 760; filled diamonds, 789; and filled circles, 2764. 'E' is aqueous vehicle control, with an AUC of 126 mg·week.

Results of the duration of androgenic activity test are shown in FIG. 7-8. Each data point represents the mean (n=5) and standard error of the mean (SEM) prostate weight for each time period. FIG. 7 shows ventral prostate weights at weekly intervals over a 14-week period following a single subcutaneous injection of 0.6 and 1.2 mg of the dimethandrolone 17-methylcarbonate (CDB-4718) and the dimethandrolone 17-decylcarbonate (CDB-4719) as aqueous microcrystalline suspensions. In FIG. 8, the data for 1.2 mg dose groups are shown together with historical data for testosterone undecanoate in aqueous suspension and testosterone enanthate in sesame oil as standards. Both testosterone undecanoate and testosterone enanthate are commercially available. CDB-4719 (2c) in aqueous suspending vehicle exhibited the most dramatic increase and maintenance of ventral prostate weight with the area under the curve (AUC) for the 14-week observation period calculated as 2764 mg·weeks. This was more than three times greater than that for the commercial preparation of testosterone enanthate in sesame oil (AUC=760) and more than five times greater than that for testosterone undecanoate (AUC=494).

CDB-4730 (2d), the dodecylcarbonate, but not CDB-4731 (2b), the hexylcarbonate, exhibited similar long-acting activity. CDB-4719 (2c) and 4730 (2d) remain at the injection site following administration as a microcrystalline aqueous suspension forming a depot from which the drug is slowly leached. Hydrolysis to the corresponding free alcohol probably occurs prior to binding to tissue specific androgen receptors and the initiation of transcription and pharmacological activity.

Figure 9:
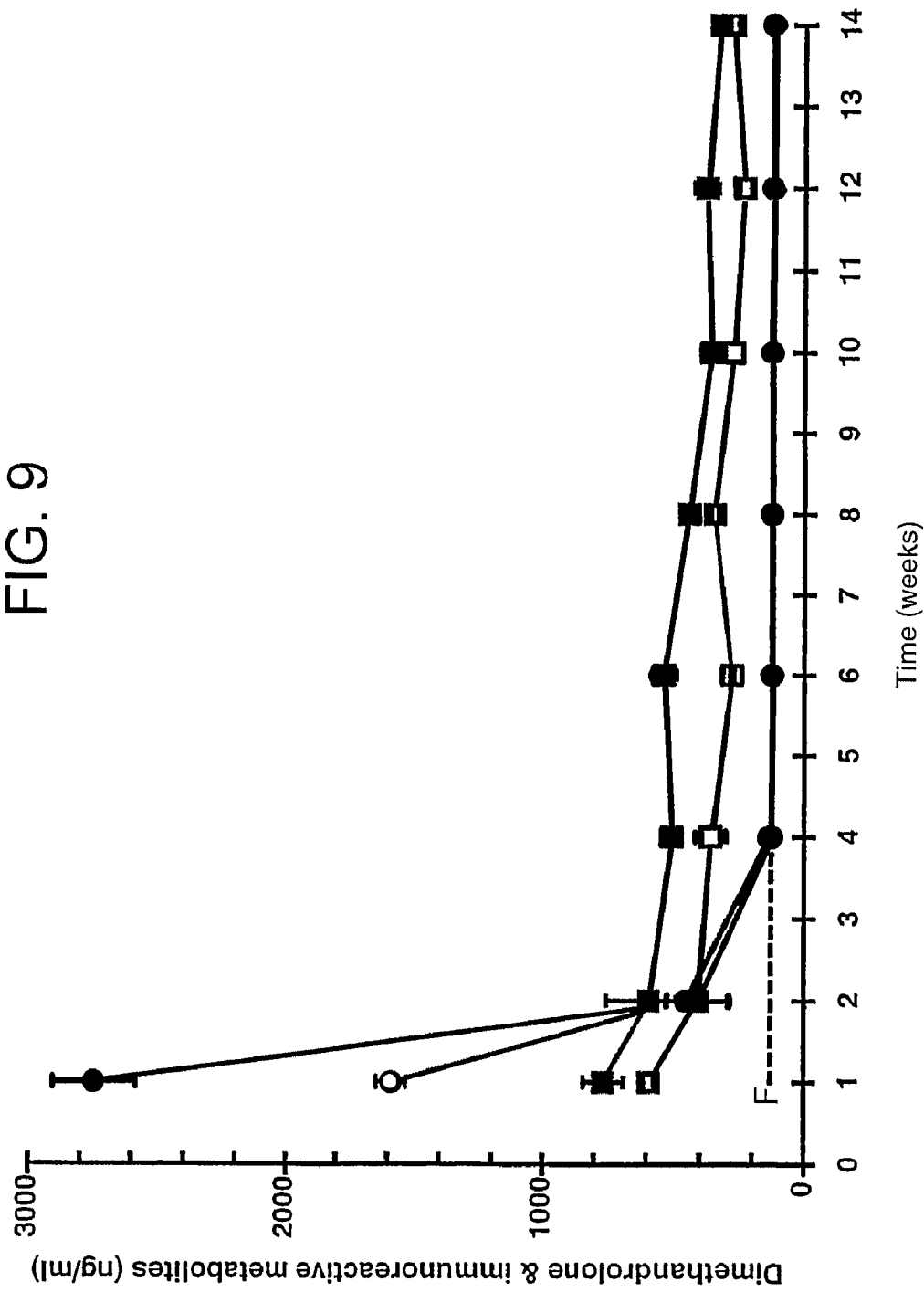
FIG. 9 depicts the serum concentration of dimethandrolone and immunoreactive metabolites following a single subcutaneous injection to castrate Sprague-Dawley male rats of 1.2 mg of CDB-4718 (2a, open circles, 0.6 mg; filled circles, 1.2 mg), CDB-4719 (2c, open squares, 0.6 mg; filled squares, 1.2 mg) in an aqueous suspending vehicle (n=5). The AUC's (mg·week) were as follows: open circles, 2848; filled circles, 3336; open squares, 4151; and filled squares, 6010. 'F' is aqueous vehicle control, with an AUC of 1590 mg·week.

FIG. 9 depicts the serum concentration of dimethandrolone and immunoreactive metabolites following a single subcutaneous injection to castrate Sprague-Dawley rats of 1.2 mg of CDB-4718 (2a, open circles, 0.6 mg; filled circles, 1.2 mg), CDB-4719 (2c, open squares, 0.6 mg; filled squares, 1.2 mg) in an aqueous suspending vehicle (n=5). The AUC's (area under the curves, mg·week) were as follows: open circles, 2848; filled circles, 3336; open squares, 4151; and filled squares, 6010. 'F' is aqueous control vehicle, with an AUC of 1590 mg·week.

Figure 10A:
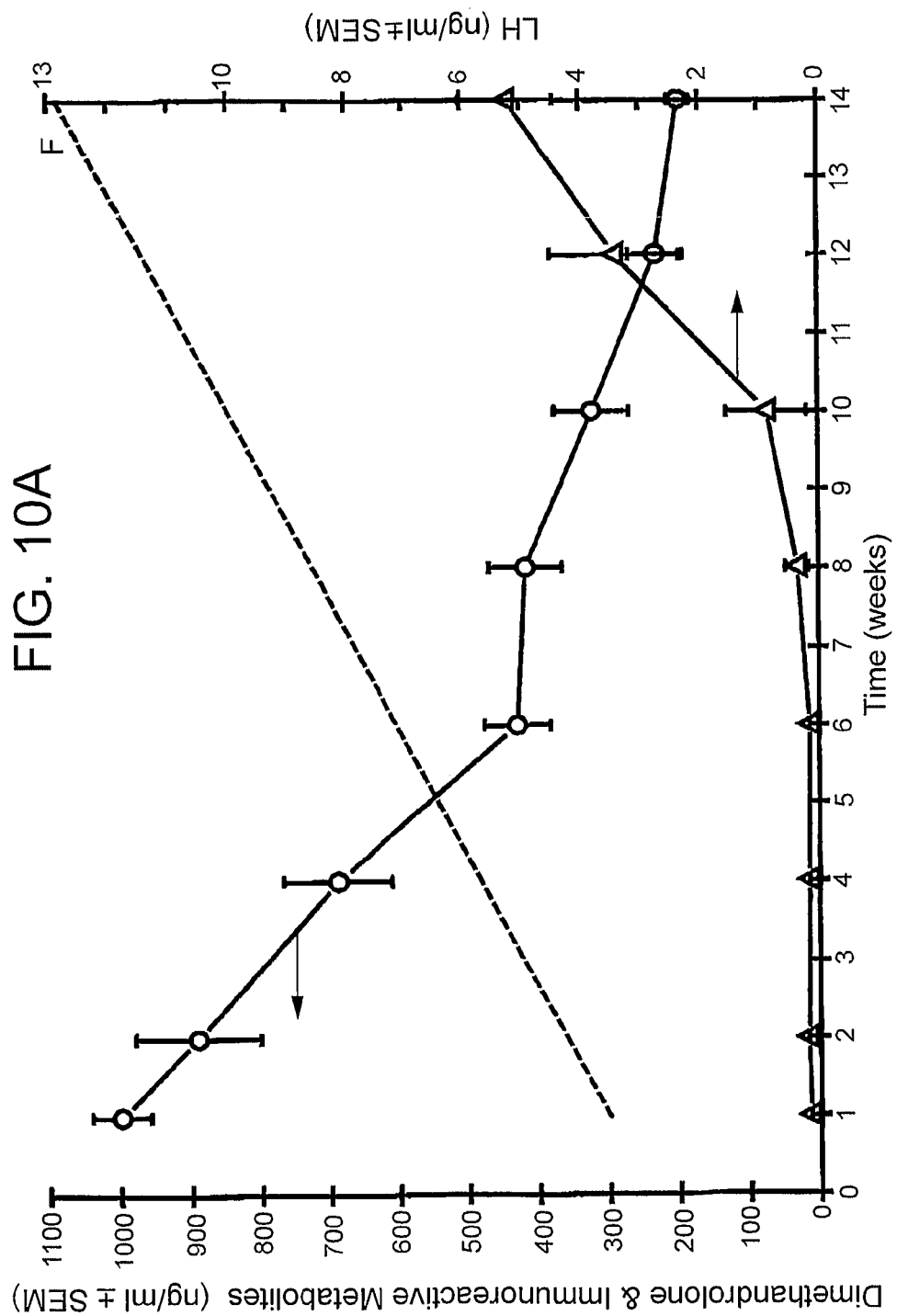
FIG. 10A depicts the serum concentration of dimethandrolone and immunoreactive metabolites and luteinizing hormone (rLH) during the 14-week period following a single subcutaneous injection of CDB-4730 (2d) to castrate Sprague-Dawley rats as an aqueous crystalline suspension. Open circles, dimethandrolone and immunoreactive metabolites, facing the Y-axis on the left; open triangles represent the serum level of rLH, facing the Y-axis on the right. The dotted line 'F' represents the vehicle control for rLH. The limit of detection of rLH and dimethandrolone was 0.18 ng/ml; n=5.
Figure 10B:
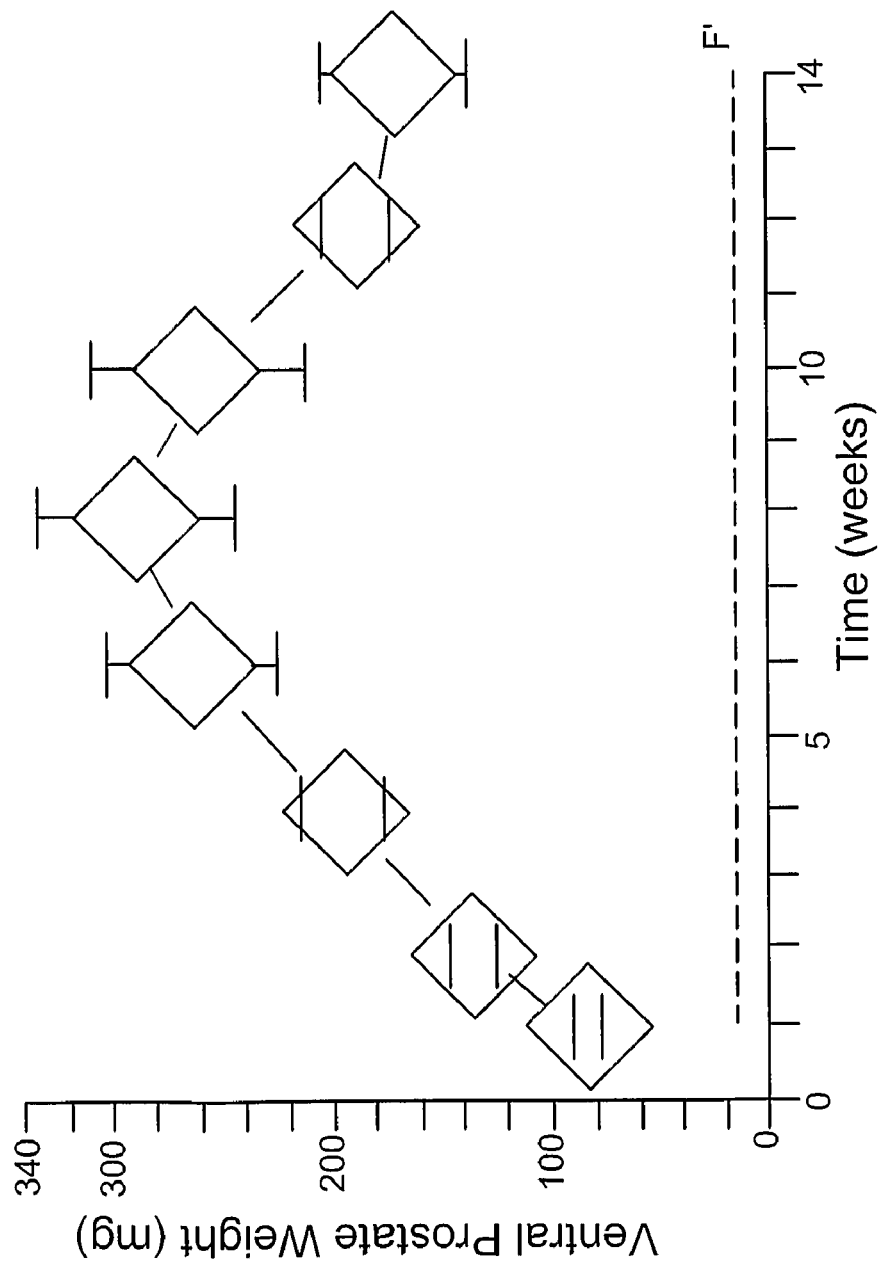
FIG. 10B depicts the androgenic activity during the 14-week period.

Serum samples from rats taken at autopsy showed the presence of the free alcohol as measured by a highly specific radioimmunoassay, which decreased with time over the 14-week observation period (FIG. 10A-B). The free alcohol itself produced serum levels barely above the limit of detection of 63 pg/ml during the first 3 weeks.

Figure 11:
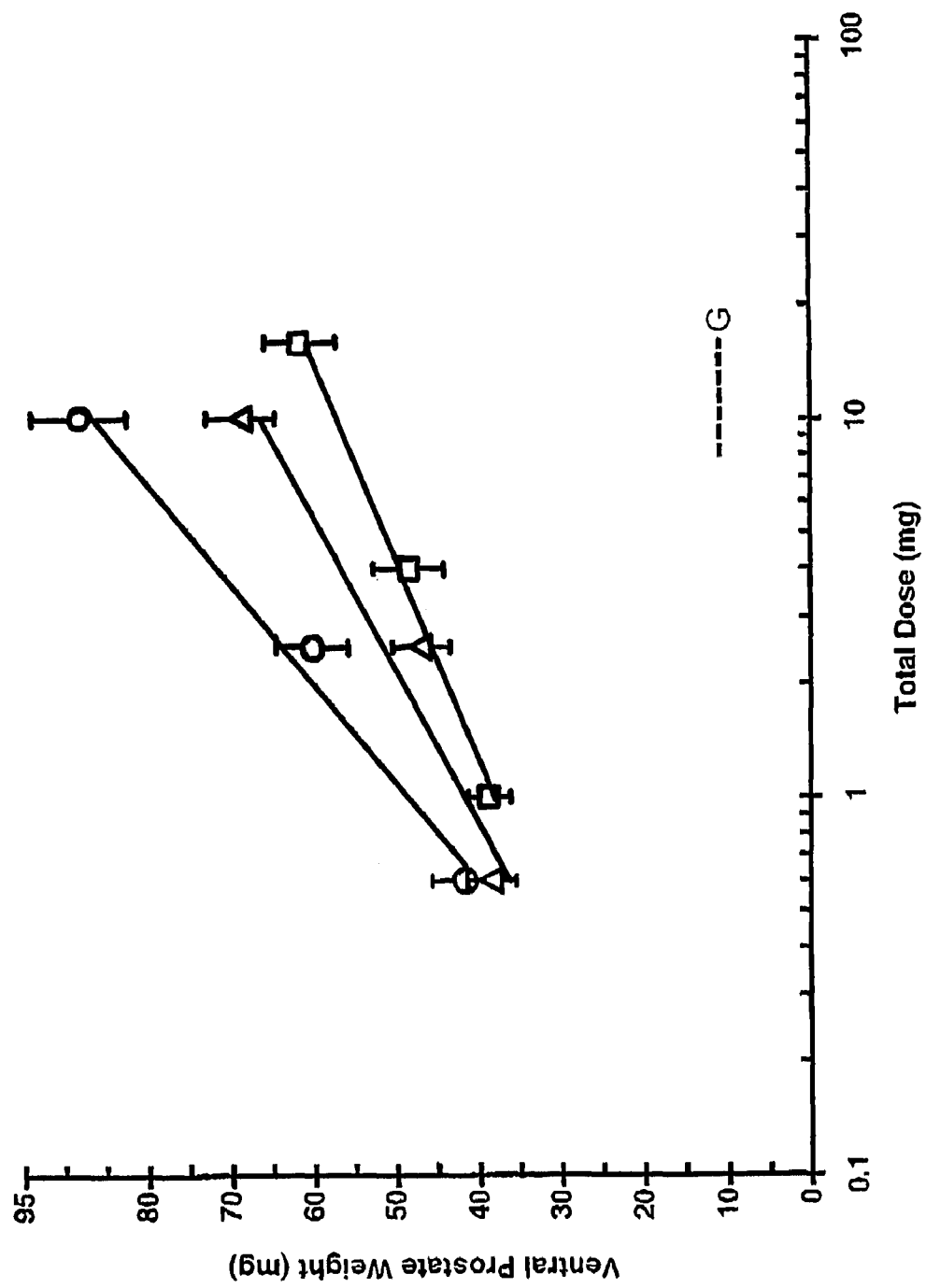
FIG. 11 depicts the androgenic activity of CDB-4757 (8a, open triangles) following oral administration of the compound to castrate Sprague-Dawley male rats in 10% ethanol/sesame oil. Open circle represents dimethandrolone decanoate and open triangles represent methyltestosterone standard. 'G' is vehicle control.

FIG. 11 shows the androgenic activity (ventral prostate weight) as a function of dose of CDB-4757, 11β-methyl-19-nortestosterone 17β-decylcarbonate. The androgenic activities of CDB-4756 (dimethandrolone decanoate) and CDB-110B (methyltestosterone standard) are also shown. The potency ratio and 95% confidence index are set forth below.

| | BIOLOGICAL ACTIVITY | |
|---|---|---|
| DRUG | Potency Ratio | 95% C.I. |
| CDB-119B | 1.00 (assigned) | |
| CDB-4756 | 2.13-7.56 | — |
| CDB-4757 | 1.96 | 1.04-367 |

Figure 12:
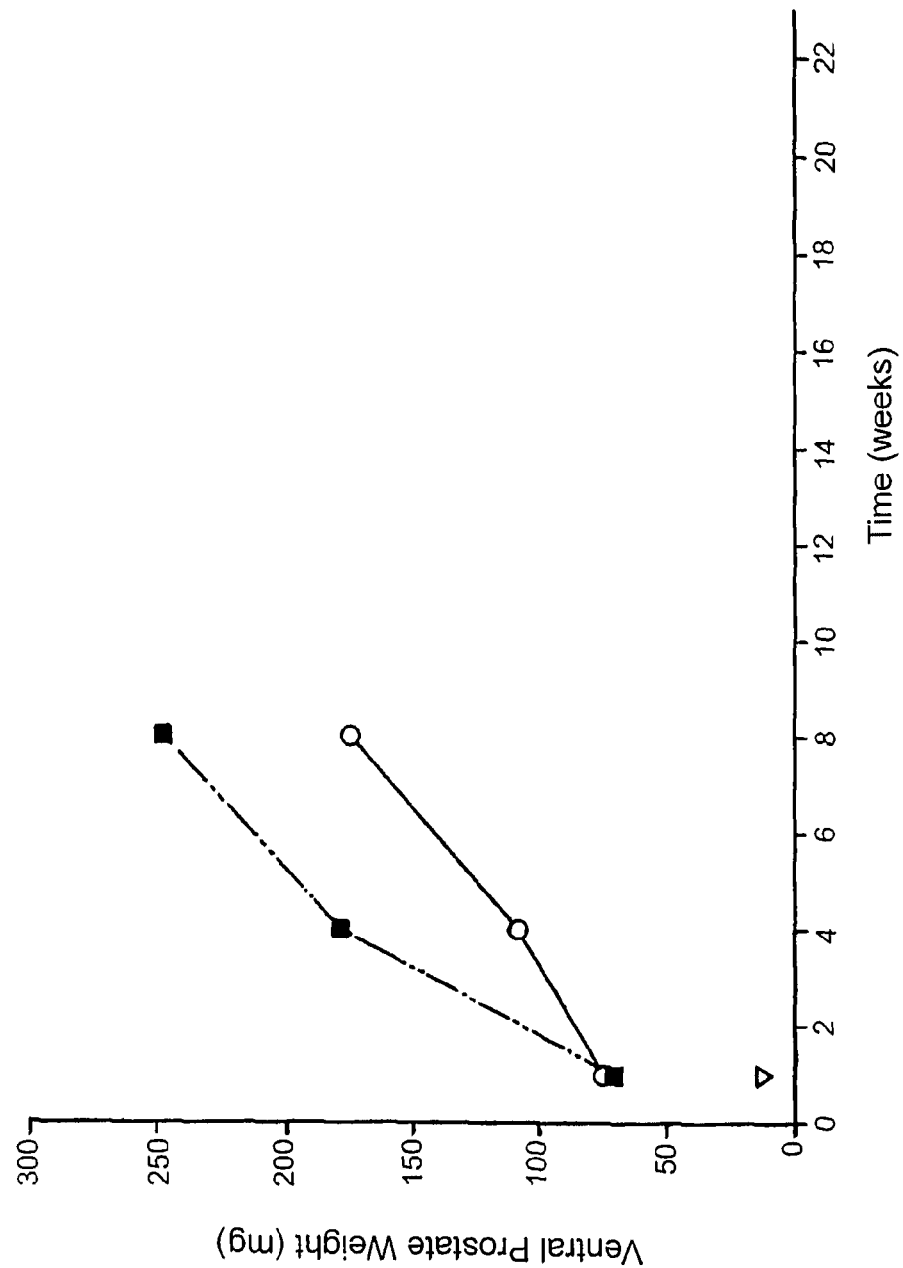
FIG. 12 shows the duration of androgenic activity of CDB-4719 (2c) and 4730 (2d) over a period of 8 weeks following a single dose (1.2 mg) administered by subcutaneous injection to castrate Sprague-Dawley male rats in an aqueous suspending vehicle on week 0. The triangle represents vehicle control (aqueous suspending vehicle).

FIG. 12 shows the duration of androgenic activity of CDB-4719 (2c) and 4730 (2d) over a period of 8 weeks following a single dose administered by subcutaneous injection in an aqueous suspending vehicle on week 0.

Figure 13:
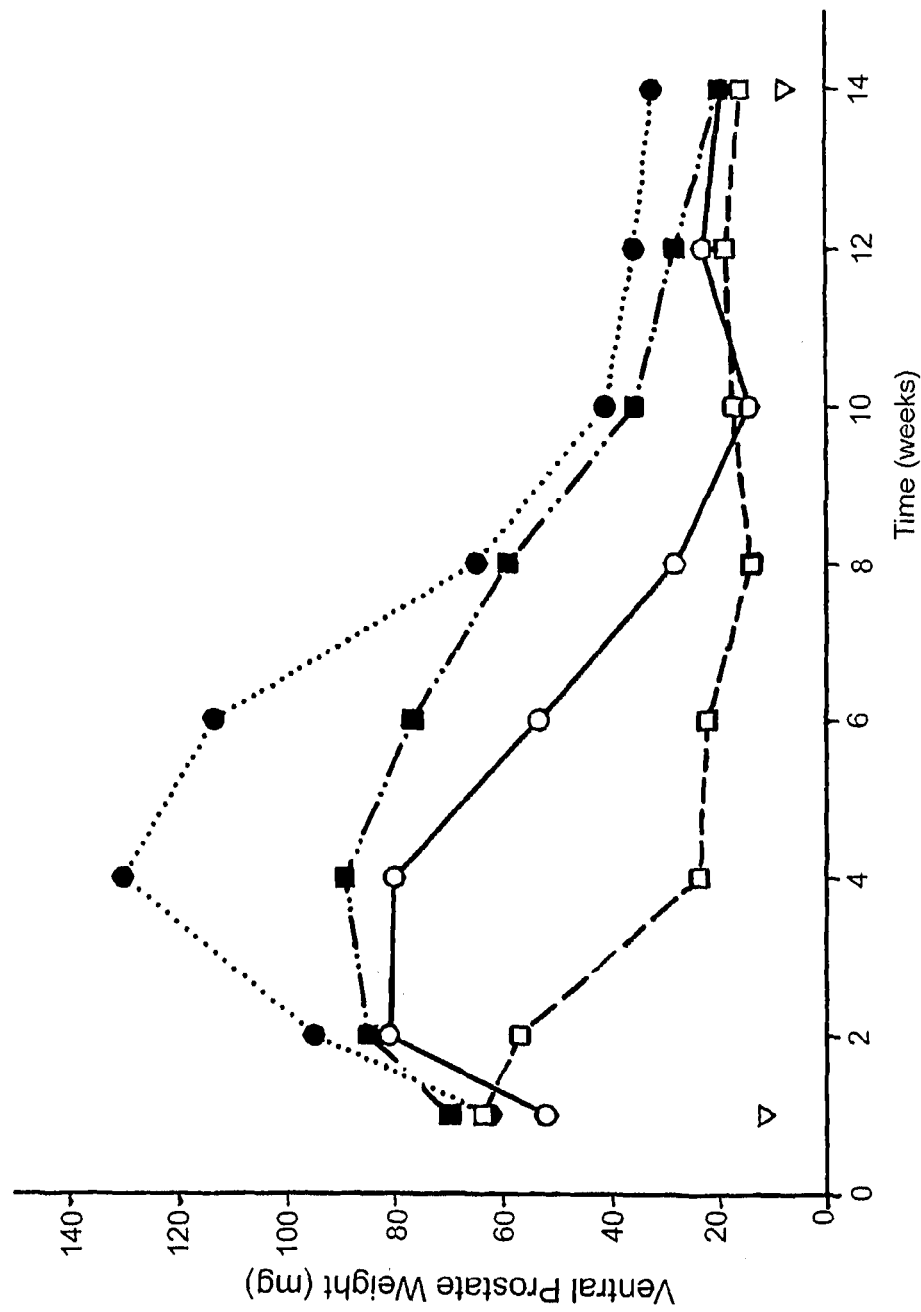
FIG. 13 shows the duration of androgenic activity of CDB-4754 (8b) and 4750A (4c), $\Delta^{14}$-dimethandrolone-17β-adamantylcarbonate) over a period of 14 weeks following a single dose (0.6 mg or 1.2 mg) administered by subcutaneous injection to castrate Sprague-Dawley male rats in an aqueous suspending vehicle on week 0. Filled circles represent CDB-4754, 1.2 mg. Filled squares represent CDB-4750A, 1.2 mg. Open circles represent CDB-4754, 0.6 mg. Open squares represent CDB-4750A, 0.6 mg. Open triangle represents aqueous suspending vehicle control. The AUC's (mg·week) were as follows: CDB-4754 0.6 mg, 564; CDB-4754 1.2 mg, 974; CDB-4750A, 0.6 mg 326; and CDB-4750A, 1.2 mg, 759.

FIG. 13 shows the duration of androgenic activity of CDB-4754 (8b) and 4750A (4c) over a period of 14 weeks following a single dose administered by subcutaneous injection on week 0. The AUC (mg·week) were as follows: CDB-4754, 0.6 mg, 564; CDB-4754, 1.2 mg, 974; CDB-4750A, 0.6 mg, 326; and CDB-4750A, 1.2 mg, 759.

Figure 14:
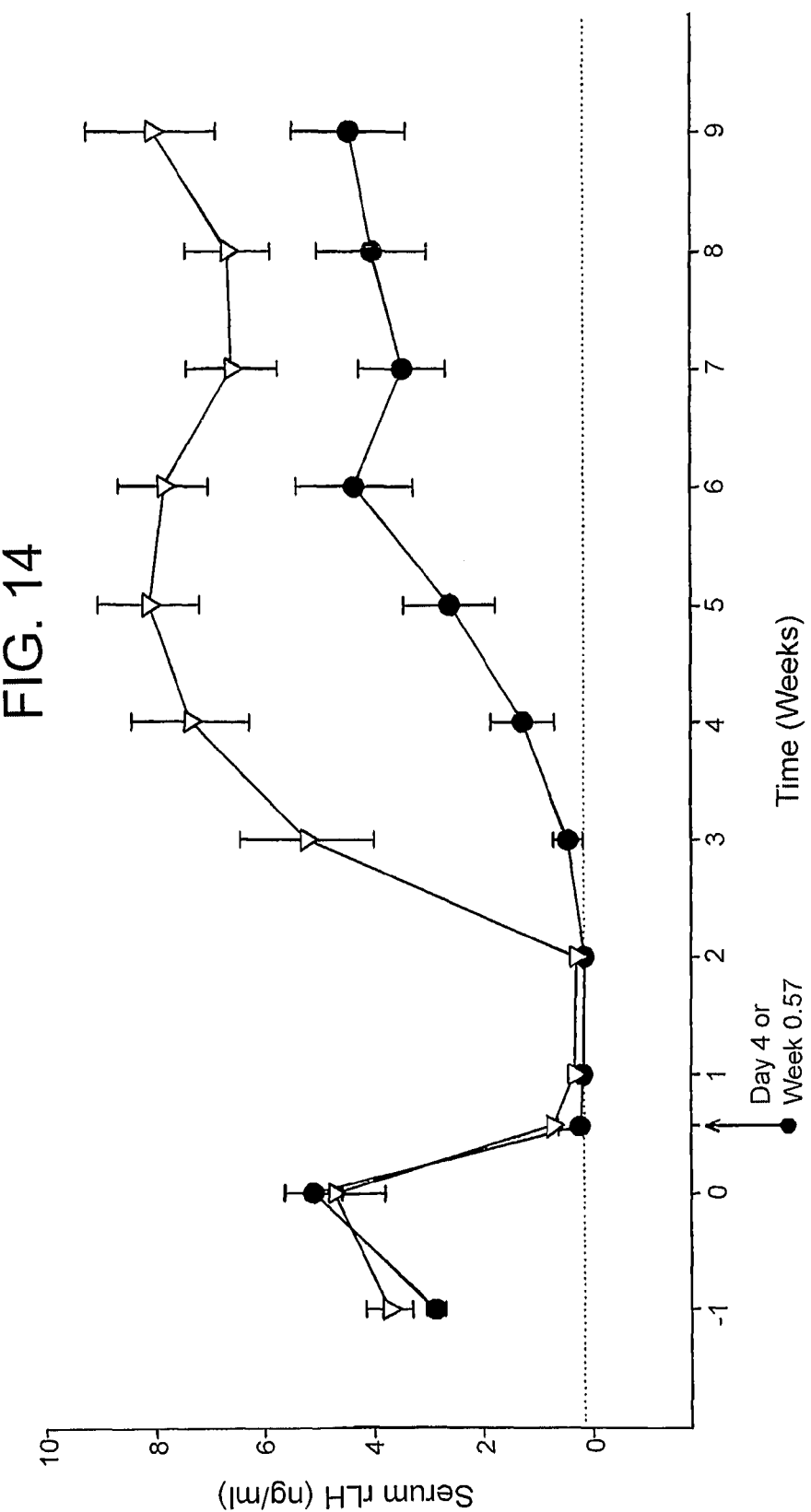
FIG. 14 depicts the serum levels of rLH as a function of time for groups 2 and 4 of the animals. Serum rLH were measured in the blood from castrate male rats following fourteen daily 12 mg/kg oral doses of CDB-4719A (dimethandrolone 17β-decylcarbonate, filled circles, group 2) or CDB-4521C (dimethandrolone 17β-undecanoate, open triangles, group 4) in 10% ethanol/sesame oil on days 0-13. Samples from weeks −1 to 6 or from weeks 7 to 9 and repeats were assayed as described in the protocols MEL-480AD using [$^{125}$I]-rLH or MEL-480AE, AG using [$^{125}$I]-rLH. The limit of detection shown as dotted line, or $EC_{90}$, was the mean of 0.13, 0.14, or 0.16 in the first assay and 0.17, 0.22, or 0.21 ng/ml in the second series of assays based on 200 µl of serum per tube.

Carbonates of the invention, in embodiments, can be used to suppress luteinizing hormone in a mammal for extended periods of time. This is illustrated in FIG. 14, which shows that serum levels of the hormone remains suppressed for several weeks even after the administration of a carbonate of the invention was stopped. CDB-4719A (dimethandrolone 17β-decylcarbonate) was administered to castrate male rats, daily at 12 mg/kg oral doses, and CDB-4521C (dimethandrolone 17β-undecanoate) was administered in 10% ethanol/sesame oil, on days 0-13. The serum level of the hormone remained suppressed for both groups of animals during the administration of the drug. When the administration of the drug was discontinued, the hormone level, as expected, bounced back and increased beyond the pretreatment level (at week −1 or 0) for the ester drug. However, with the carbonate, unexpectedly and surprisingly, the hormone level remained suppressed for several weeks. This observation could have advantageous clinical implications, for example, in obtaining sustained suppression of the luteinizing hormone or hormone replacement therapy. In addition, this could have an advantage by providing a facile treatment using oral compositions such as tablets or capsules of the carbonates of the invention in suppressing hormone levels. Such treatment can be advantageous relative to a treatment involving parenteral (e.g., subcutaneous) administration of a drug such as the ester drug. Patient compliance is better with oral formulations than injections.

Figure 15:
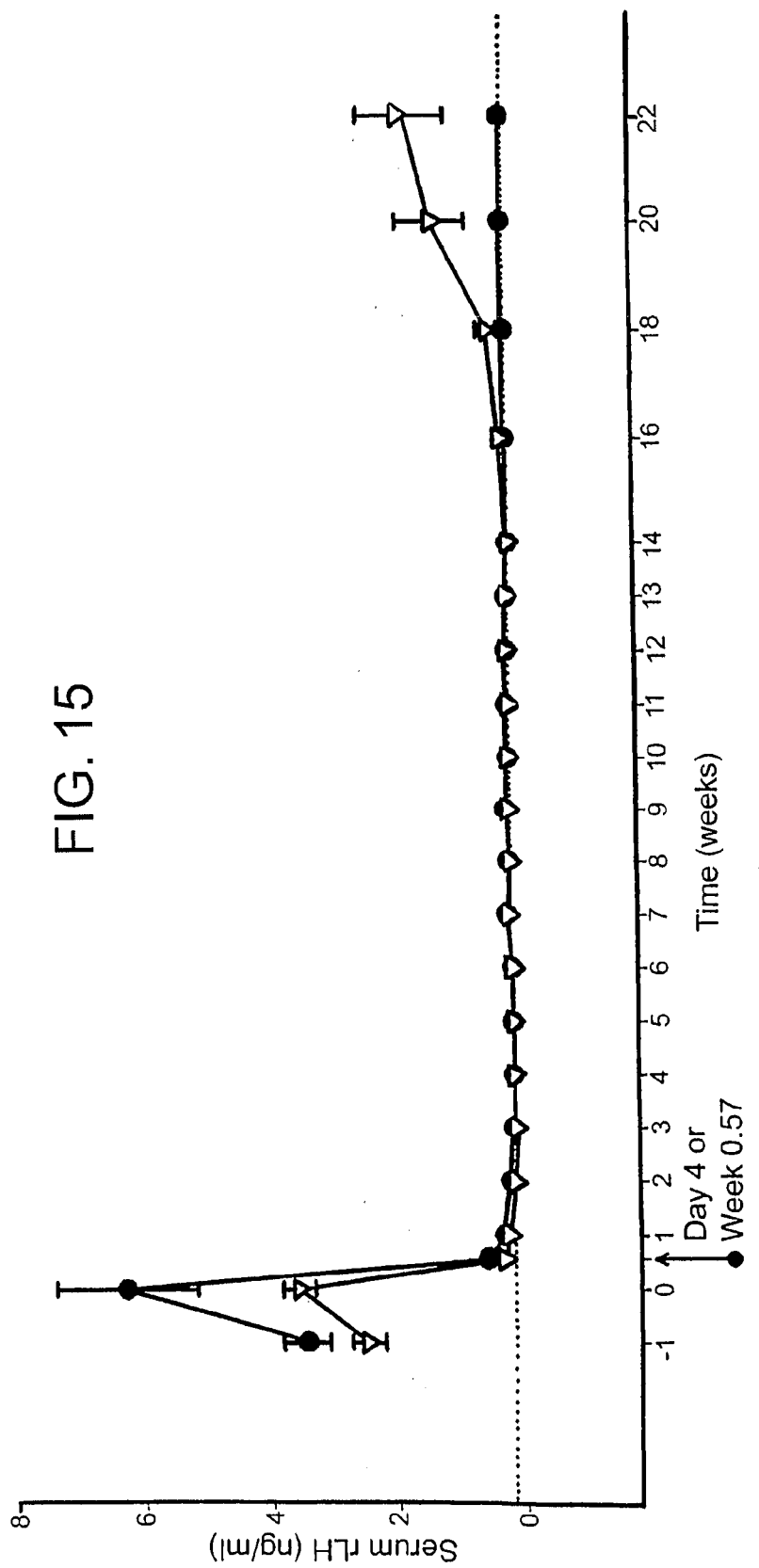
FIG. 15 depicts the serum levels of rLH as a function of time for groups 1 and 3 of the animals. Serum rLH were measured in the blood from castrate male rats following a single 12 mg/kg subcutaneous injection of CDB-4719A (dimethandrolone 17β-decylcarbonate, filled circles, group 1) or CDB-4521C (dimethandrolone 17β-undecanoate, open triangles, group 3) in an aqueous suspending vehicle on day 0. Samples from weeks −1 to 6 or from weeks 7 to 22 and repeats were assayed as described in the protocols MEL-480AD using [$^{125}$I]-rLH or MEL-480AE, AG, AH using [$^{125}$I]-rLH. The limit of detection shown as dotted line, or $EC_{90}$, was the mean of 0.13, 0.14, or 0.16 in the first assay and 0.17, 0.22, or 0.21 ng/ml in the second series of assays based on 200 µl of serum per tube.

FIG. 15 provides a comparison between CDB-4719A (dimethandrolone 17β-decylcarbonate) and CDB-4521C (dimethandrolone 17β-undecanoate). A single dose (12 mg/kg) of the compound was administered to castrate male rats by subcutaneous injection in an aqueous suspending vehicle on day 0. The serum rLH concentration was monitored over a 22-week period and beyond. Up to 16 weeks post administration, the serum level remains suppressed. The serum hormone level rose after 16 weeks for the undecanoate but the serum hormone level remained past the 16-week period for the carbonate. The serum level remained suppressed even at week 22.

Figure 16:
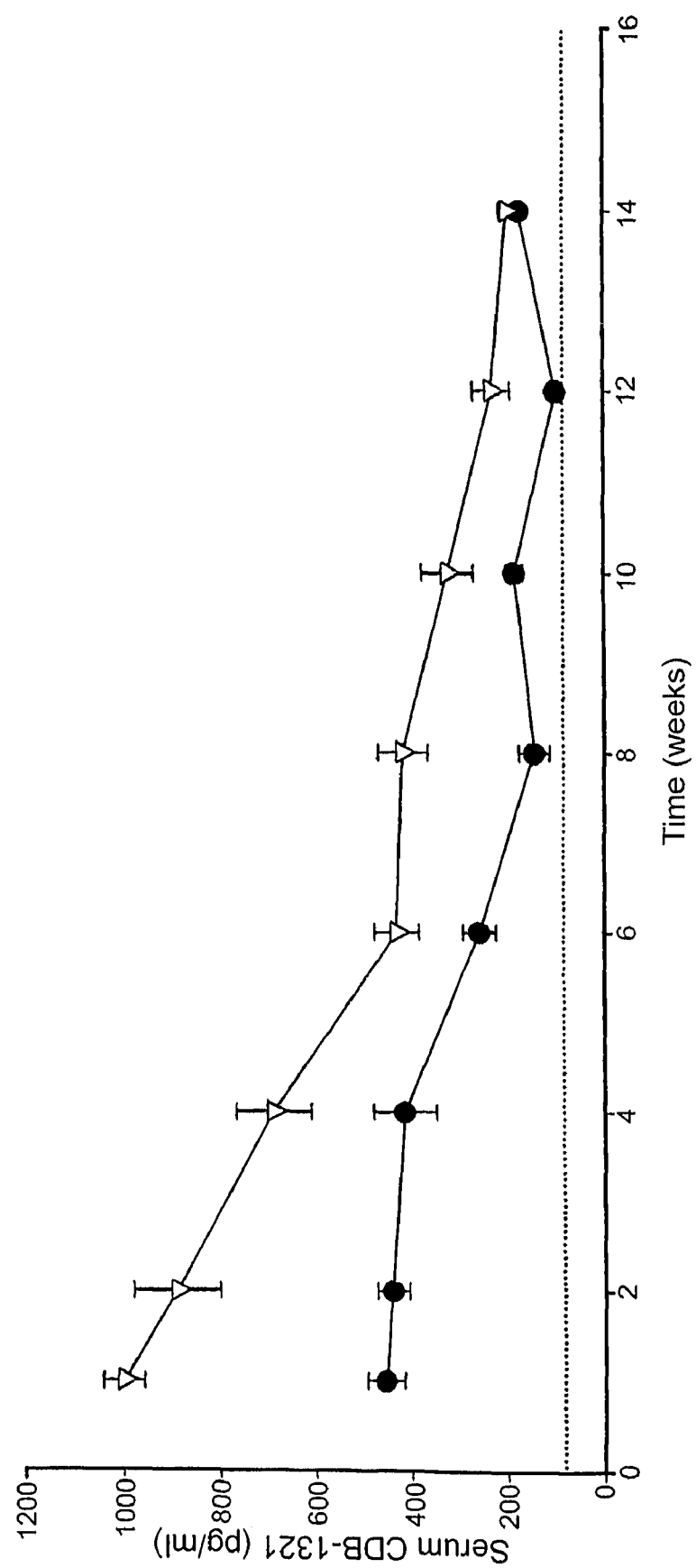
FIG. 16 depicts the serum levels of dimethandrolone (CDB-1321) and immunoreactive metabolites from castrate immature male rats given a single subcutaneous dose of 0.6 (filled circles) or 1.2 mg (open triangles) per rat of CDB-4730 (dimethandrolone 17β-dodecylcarbonate) in an aqueous suspending vehicle. The limit of detection, shown in dotted line, was 82.0 pg/ml (100 µl of serum per tube) calculated from the mean±3 SD of the vehicle control samples from weeks 1 and 14 (n=10).

In another experiment, the serum levels of CDB-1321 (dimethandrolone) and immunoreactive metabolites were monitored after the administration of a single subcutaneous dose of CDB-4730 (dimethandrolone 17β-dodecylcarbonate) in an aqueous suspending vehicle. FIG. 16 shows that the serum levels of dimethandrolone and immunoreactive metabolites decreased with time as expected.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of formula (I):

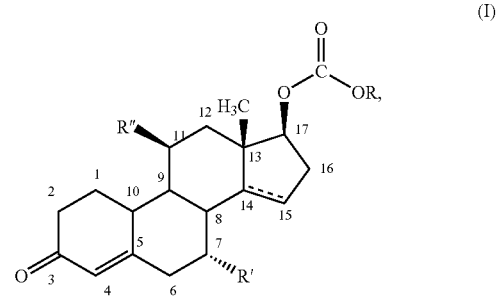

wherein R is a $C_1$-$C_{30}$ alkyl which may be optionally further substituted with one or more $C_5$-$C_8$ cycloalkyl groups or a $C_5$-$C_{12}$ cycloalkyl which may be optionally substituted with one or more $C_1$-$C_{30}$ alkyl groups; R' is hydrogen or lower alkyl; R" is a $C_1$-$C_{30}$ alkyl or halo; and the bond between C14 and C15 can be a single bond or double bond.

2. The compound of claim 1, wherein R' is methyl or ethyl.

3. The compound of claim 1, wherein R" is a $C_1$-$C_{30}$ alkyl.

4. The compound of claim 3, wherein R" is $C_1$-$C_6$ alkyl.

5. The compound of claim 4, wherein R" is methyl or ethyl.

6. The compound of claim 1, wherein R is $C_1$-$C_{30}$ alkyl.

7. The compound of claim 6, wherein R is $C_1$-$C_{18}$ alkyl.

8. The compound of claim 7, wherein R is $C_1$-$C_{12}$ alkyl.

9. The compound of claim 1, wherein the bond between C14 and C15 is a single bond.

10. The compound of claim 9, wherein R' is hydrogen.

11. The compound of claim 10, which is selected from the group consisting of 11β-ethyl-19-nortestosterone-17-methylcarbonate, 11β-ethyl-19-nortestosterone-17-decylcarbonate, 11β-ethyl-19-nortestosterone-17-dodecylcarbonate, 11β-methyl-19-nortestosterone-17-methylcarbonate, 11β- methyl-19-nortestosterone-17-decylcarbonate, and 11β-methyl-19-nortestosterone-17-(trans-4-n-butylcyclohexyl) carbonate.

12. The compound of claim 9, wherein R" is a halogen.

13. The compound of claim 12, which is selected from the group consisting of 11β-fluoro-19-nortestosterone-17-decylcarbonate, 11β-fluoro-19-nortestosterone-17-dodecylcarbonate, 11β-chloro-19-nortestosterone-17-decylcarbonate, 11β-chloro-19-nortestosterone-17-dodecylcarbonate, and 11β-fluoro-19-nortestosterone-17-(trans-4-n-butylcyclohexyl) carbonate.

14. The compound of claim 9, which is selected from the group consisting of 7α-methyl, 11β-ethyl-19-nortestosterone-17-methylcarbonate, 7α-methyl, 11β-ethyl-19-nortestosterone-17-decylcarbonate, 7α-methyl, 11β-ethyl-19-nortestosterone-17-dodecylcarbonate, 7α, 11β-dimethyl-19-nortestosterone-17-methylcarbonate, 7α, 11β-dimethyl-19-nortestosterone-17-hexylcarbonate, 7α, 11β-dimethyl-19-nortestosterone-17-decylcarbonate, and 7α, 11β-dimethyl-19-nortestosterone-17-dodecylcarbonate.

15. The compound of claim 9, which is selected from the group consisting of 7α-ethyl, 11β-methyl-19-nortestosterone-17-methylcarbonate, 7α-ethyl, 11β-methyl-19-nortestosterone-17-hexylcarbonate, 7α-ethyl, 11β-methyl-19-nortestosterone-17-decylcarbonate, 7α-ethyl, 11β-methyl-19-nortestosterone-17-dodecylcarbonate, 7α, 11β-diethyl-19-nortestosterone-17-methylcarbonate, 7α, 11β-diethyl-19-nortestosterone-17-hexylcarbonate, 7α, 11β-diethyl-19-nortestosterone-17-decylcarbonate, 7α, 11β-diethyl-19-nortestosterone-17-dodecylcarbonate, 11β-methyl-19-nortestosterone-17-(trans-4-n-butylcyclohexyl) carbonate, and 7α, 11β-dimethyl-19-nortestosterone-17-(trans-4-n-butylcyclohexyl) carbonate.

16. The compound of claim 9, wherein R' is methyl or hydrogen and R" is halogen.

17. The compound of claim 16, which is selected from the group consisting of 7α-methyl, 11β-fluoro-19-nortestosterone-17-decylcarbonate, 7α-methyl, 11β-fluoro-19-nortestosterone-17-dodecylcarbonate, 7α-methyl, 11β-chloro-19-nortestosterone-17-decylcarbonate, and 7α-methyl, 11β-chloro-19-nortestosterone-17-dodecylcarbonate, and 11β-fluoro-19-nortestosterone-17-(trans-4-n-butylcyclohexyl) carbonate.

18. The compound of claim 9, wherein R is decyl or dodecyl.

19. The compound of claim 9, wherein R" is methyl or ethyl.

20. The compound of claim 9, wherein R" is a halogen.

21. The compound of claim 9, wherein R" is chloro or fluoro.

22. The compound of claim 1, wherein R is $C_5$-$C_{12}$ cycloalkyl.

23. The compound of claim 22, wherein the cycloalkyl is a tricycloalkyl.

24. The compound of claim 23, wherein the tricycloalkyl is $C_{10}$ tricycloalkyl.

25. The compound of claim 1, wherein the bond between C14 and C15 is a double bond.

26. The compound of claim 25, which is 7α, 11β-dimethyl-14-dehydro-19-nortestosterone-17-adamantylcarbonate.

27. The compound of claim 25, wherein R is $C_1$-$C_{18}$ alkyl.

28. The compound of claim 27, wherein R is $C_1$-$C_{12}$ alkyl.

29. The compound of claim 28, wherein R is methyl.

30. The compound of claim 28, wherein R is decyl.

31. A pharmaceutical composition comprising a compound of claim 1, and a pharmaceutically acceptable carrier.

32. The pharmaceutical composition of claim 31, which is suitable for oral administration.

33. The pharmaceutical composition of claim 31, which is suitable for parenteral administration.

34. A pharmaceutical composition comprising a compound of claim 11 and a pharmaceutically acceptable carrier, wherein the composition is suitable for oral administration.

35. The pharmaceutical composition of claim 34, wherein the compound is 7α, 11β-dimethyl-19-nortestosterone-17-decylcarbonate.

36. A pharmaceutical composition comprising the compound of claim 11 and a pharmaceutically acceptable carrier, wherein the composition is suitable for subcutaneous injection.

37. The pharmaceutical composition of claim 36, wherein the compound is 7α, 11β-dimethyl-19-nortestosterone-17-methylcarbonate or 7α, 11β-dimethyl-19-nortestosterone-17-hexylcarbonate.

38. A pharmaceutical composition comprising an aqueous crystalline suspension of a compound of claim 11, wherein the composition is suitable for subcutaneous injection.

39. The pharmaceutical composition of claim 38, wherein the compound is 7α, 11β-dimethyl-19-nortestosterone-17-decylcarbonate.

40. A method for treating a male patient for hypogonadism comprising administering an effective amount of a compound of claim 1.

41. The method of claim 40, wherein the hypogonadism is selected from the group consisting of hypogonadotropic eunuchoidism, fertile eunuch syndrome, prepubertal panhypopituitarism, and postpubertal pituitary failure, and any combination thereof.

42. The method of claim 40, wherein the hypogonadism is selected from the group consisting of Klinefelter's syndrome, Reifenstein's syndrome, functional prepubertal castration syndrome, male "Turner's syndrome", Sertoli cell-only syndrome, adult seminiferous tubule failure, and adult Leydig cell failure, and any combination thereof.

43. A method for providing hormonal therapy to a patient comprising administering an effective amount of a compound of claim 1.

44. A method for providing a contraceptive to a male comprising administering to the male an effective amount of a compound of claim 1.

45. A method for treating a patient with osteoporosis comprising administering an effective amount of a compound of claim 1.

46. A method for treating a patient with anemia comprising administering an effective amount of a compound of claim 1.

47. A method for promoting and maintaining muscle growth in a patient in need thereof comprising administering an effective amount of a compound of claim 1.

48. The method of claim 47, wherein the patient is afflicted with a muscle wasting disease.

49. The method of claim 48, wherein the muscle wasting disease is AIDS.

50. The method of claim 47, wherein the patient is afflicted with cancer.

51. A method of suppressing the release of luteinizing hormone in a mammal comprising administering to the mammal an effective amount of 7α, 11β-dimethyl-19-nortestosterone-17-decylcarbonate.

52. The compound of claim 1, wherein R' is hydrogen, R" is methyl, R is dodecyl, and the bond between C14 and C15 is a single bond.

53. A pharmaceutical composition comprising the compound of claim 52 and a pharmaceutically acceptable carrier.

54. A method of treating a male patient for hypogonadism comprising administering an effective amount of the compound of claim 52.

55. The method of claim 54, wherein the hypogonadism is selected from the group consisting of hypogonadotropic eunuchoidism, fertile eunuch syndrome, prepubertal panhypopituitarism, and postpubertal pituitary failure, and any combination thereof.

56. The method of claim 54, wherein the hypogonadism is selected from the group consisting of Klinefelter's syndrome, Reifenstein's syndrome, functional prepubertal castration syndrome, male "Turner's syndrome", Sertoli cell-only syndrome, adult seminiferous tubule failure, and adult Leydig cell failure, and any combination thereof.

57. A method for providing a contraceptive to a male comprising administering to the male an effective amount of a compound of claim 52.

58. A method for treating a patient with osteoporosis comprising administering an effective amount of a compound of claim 52.

59. A method for treating a patient with anemia comprising administering an effective amount of a compound of claim 52.

60. A method for promoting and maintaining muscle growth in a patient in need thereof comprising administering an effective amount of a compound of claim 52.

61. The method of claim 60, wherein the patient is afflicted with a muscle wasting disease.

62. The method of claim 61, wherein the muscle wasting disease is AIDS.

* * * * *

UNITED STATES PATENT AND TRADEMARK OFFICE
CERTIFICATE OF CORRECTION

| | | |
|---|---|---|
| PATENT NO. | : 7,820,642 B2 | Page 1 of 1 |
| APPLICATION NO. | : 11/815532 | |
| DATED | : October 26, 2010 | |
| INVENTOR(S) | : Blye et al. | |

It is certified that error appears in the above-identified patent and that said Letters Patent is hereby corrected as shown below:

Title Page item (73) which reads:

"Assignees: The United States of America as represented by the Department of Health and Human Services, Washington, DC (US)"

should read:

--The United States of America as represented by the Department of Health and Human Services, Bethesda, MD (US)--

Signed and Sealed this
Twenty-fifth Day of January, 2011

David J. Kappos
*Director of the United States Patent and Trademark Office*